US009665050B2

(12) United States Patent
Yamamoto et al.

(10) Patent No.: US 9,665,050 B2
(45) Date of Patent: May 30, 2017

(54) DETERMINATION APPARATUS FOR DETERMINING TYPE OF RECORDING MEDIUM

(71) Applicant: CANON KABUSHIKI KAISHA, Tokyo (JP)

(72) Inventors: Tetsuya Yamamoto, Suntou-gun (JP); Tsutomu Ishida, Suntou-gun (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/157,128

(22) Filed: May 17, 2016

(65) Prior Publication Data
US 2016/0259285 A1 Sep. 8, 2016

Related U.S. Application Data

(63) Continuation of application No. 14/847,256, filed on Sep. 8, 2015, now Pat. No. 9,372,461.

(30) Foreign Application Priority Data

Sep. 16, 2014 (JP) ................................. 2014-188250

(51) Int. Cl.
*G03G 15/00* (2006.01)
*G01N 29/07* (2006.01)
(Continued)

(52) U.S. Cl.
CPC ......... *G03G 15/5025* (2013.01); *G01N 29/07* (2013.01); *G01N 29/11* (2013.01);
(Continued)

(58) Field of Classification Search
USPC ..................................................... 399/45, 48
See application file for complete search history.

(56) References Cited

U.S. PATENT DOCUMENTS 5,032,975 A 7/1991 Yamamoto et al.
5,136,222 A 8/1992 Yamamoto et al.
(Continued)

FOREIGN PATENT DOCUMENTS

| JP | H03-102676 A | 4/1991 |
| JP | 2004-028994 A | 1/2004 |
| JP | 2010-018433 A | 1/2010 |

OTHER PUBLICATIONS

U.S. Appl. No. 14/939,452 by Teruhiko Maniki, et al., filed Nov. 12, 2015.

*Primary Examiner* — Clayton E Laballe
*Assistant Examiner* — Warren K Fenwick
(74) *Attorney, Agent, or Firm* — Fitzpatrick, Cella, Harper & Scinto

(57) ABSTRACT

A transmission unit transmits an ultrasonic wave by a drive signal being supplied to two terminals. A reception unit receives the ultrasonic wave transmitted from the transmission unit and to output a reception signal from two terminals in accordance with the received ultrasonic wave. A change unit changes a determination scheme for determining a type of a recording medium, based on information indicating a relation between a polar character of the transmission unit and a polar character of the reception unit, the information having been acquired from the reception signal.

24 Claims, 14 Drawing Sheets

(51) Int. Cl.
*G01N 29/24* (2006.01)
*G01N 29/11* (2006.01)

(52) U.S. Cl.
CPC ......... *G01N 29/2437* (2013.01); *G03G 15/50*
(2013.01); *G03G 15/5029* (2013.01); *G01N 2291/0237* (2013.01); *G01N 2291/048*
(2013.01); *G01N 2291/102* (2013.01)

(56) References Cited

U.S. PATENT DOCUMENTS

| | | | |
|---|---|---|---|
| 5,159,502 A | 10/1992 | Ejima et al. | |
| 5,347,545 A * | 9/1994 | Ishii | H04W 74/0816 340/2.4 |
| 5,609,154 A * | 3/1997 | Oppelt | G01S 7/523 600/453 |
| 6,078,663 A | 6/2000 | Yamamoto | |
| 6,597,790 B1 | 7/2003 | Yamamoto | |
| 6,864,747 B1 * | 3/2005 | Oppelt | H03F 1/3217 330/267 |
| 6,925,891 B2 | 8/2005 | Suginouchi et al. | |
| 7,071,865 B2 | 7/2006 | Shibamiya et al. | |
| 7,296,234 B2 | 11/2007 | Fukuda et al. | |
| 7,496,278 B2 | 2/2009 | Miyamoto et al. | |
| 7,522,087 B2 | 4/2009 | Shibamiya et al. | |
| 8,023,802 B2 | 9/2011 | Miyamoto et al. | |
| 8,391,735 B2 * | 3/2013 | Kuramochi | B65H 7/02 399/389 |
| 8,549,742 B2 | 10/2013 | Yamamoto | |
| 8,635,912 B2 * | 1/2014 | Aoki | G03G 15/6558 399/389 |
| 8,774,653 B2 | 7/2014 | Iwasa et al. | |
| 8,875,581 B2 * | 11/2014 | Nakamura | G03G 15/5029 73/599 |
| 8,884,471 B2 | 11/2014 | Yamamoto | |
| 9,058,000 B2 * | 6/2015 | Ebihara | G03G 15/5029 |
| 9,372,461 B2 * | 6/2016 | Yamamoto | G03G 15/50 |
| 2011/0142459 A1 * | 6/2011 | Aoki | G03G 15/6558 399/12 |
| 2011/0142461 A1 * | 6/2011 | Nakamura | G03G 15/5029 399/45 |
| 2011/0191568 A1 | 8/2011 | Yamamoto | |
| 2013/0039672 A1 * | 2/2013 | Ishida | G03G 15/5029 399/45 |
| 2014/0105625 A1 * | 4/2014 | Aoki | G03G 15/6558 399/45 |
| 2015/0015085 A1 | 1/2015 | Yamamoto | |
| 2015/0037053 A1 | 2/2015 | Ishida | |
| 2015/0309459 A1 * | 10/2015 | Watanabe | G03G 15/5029 399/45 |

\* cited by examiner

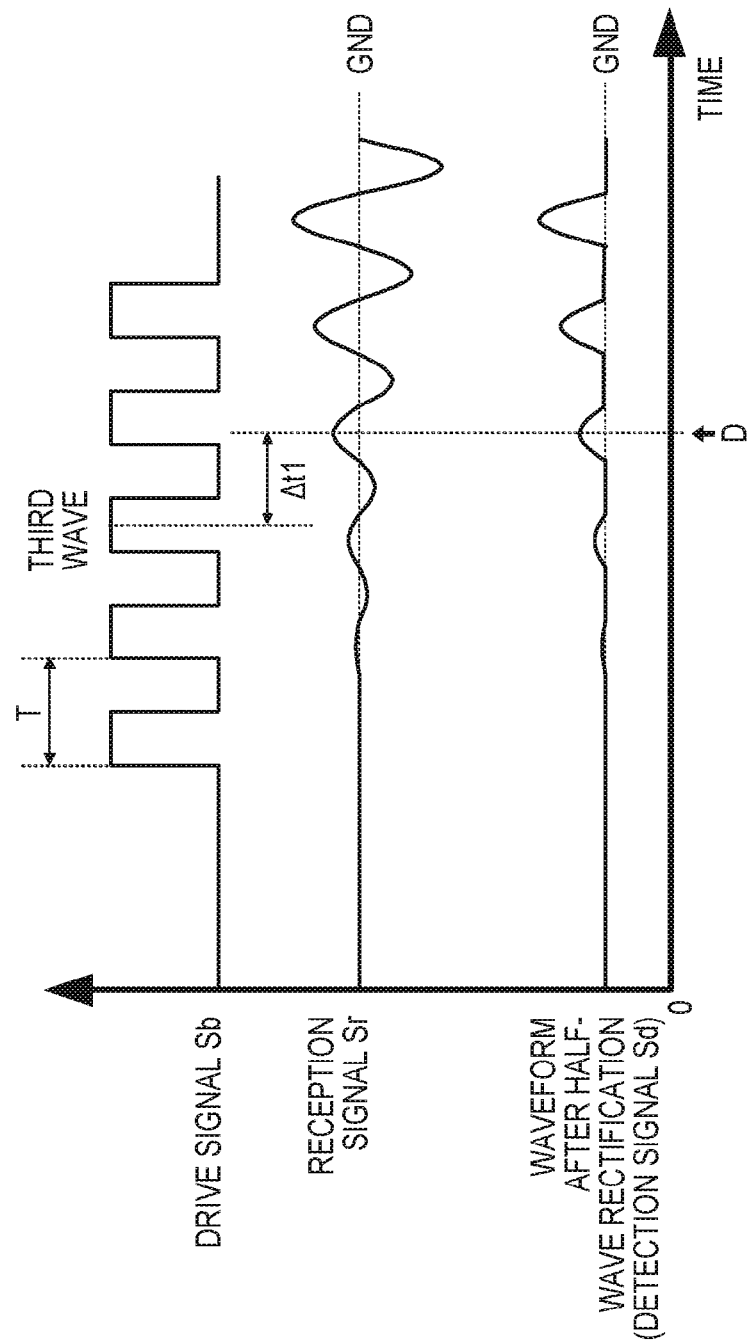

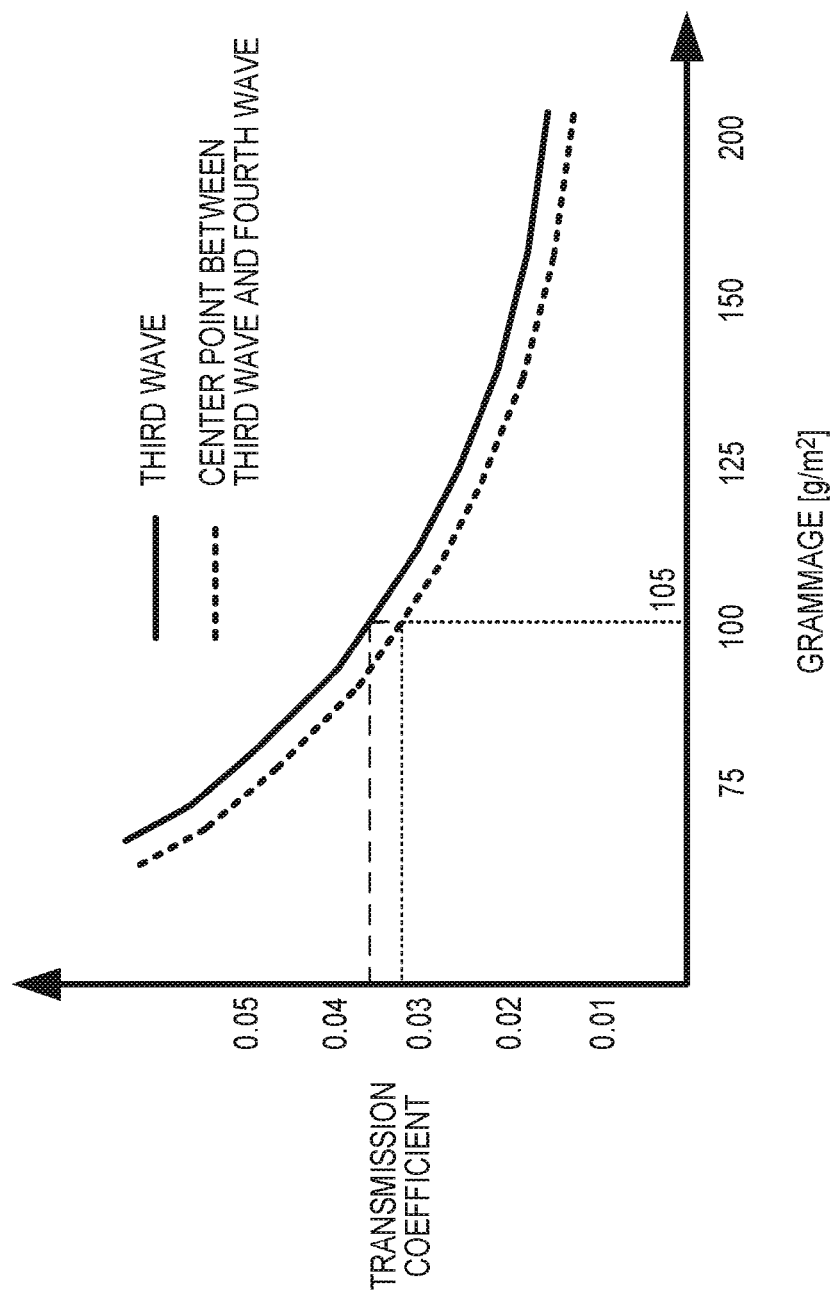

DETERMINATION APPARATUS FOR DETERMINING TYPE OF RECORDING MEDIUM

This application is a continuation of U.S. patent application Ser. No. 14/847,256 (allowed), which was filed Sep. 8, 2015, the contents of which are incorporated herein by reference.

BACKGROUND OF THE INVENTION

Field of the Invention

The present invention relates to a determination apparatus for determining the type of a recording medium and to an image forming apparatus.

Description of the Related Art

Image forming apparatuses determine the types of recording media, and set image forming conditions (transfer condition, fixing condition, etc.) in accordance with the type of the recording medium. Japanese Patent Laid-Open No. 2010-18433 proposes to irradiate a recording medium with an ultrasonic wave and detect the transmission coefficient of the ultrasonic wave that is transmitted by the recording medium so as to determine the grammage (weight per unit area) of the recording medium.

Incidentally, ultrasonic wave sensors are provided with a transmission part and a reception part, and the transmission part and the reception part are each constituted by a piezoelectric element. The terminals of the piezoelectric element have positive and negative polar characters. Whether or not the polar characters of the piezoelectric element of the transmission part and the polar characters of the piezoelectric element of the reception part match influences the determination result of a recording medium.

However, managing polar characters increases component costs and assembly costs. Moreover, managing polar characters is not required due to the use of ultrasonic waves. Therefore, many ultrasonic wave sensors serving as general purpose components whose polar characters are not managed exist in the market. Accordingly, if the type of the recording medium can be determined using the general purpose components in which the polar characters of the transmission part and the reception part are not managed, it will be possible to reduce the cost of a determination apparatus.

SUMMARY OF THE INVENTION

In view of this, the present invention reduces the cost of a determination apparatus for determining the type of a recording medium.

The present invention provides a determination apparatus comprising the following elements. A transmission unit has two terminals having a polar character and is configured to transmit an ultrasonic wave by a drive signal being supplied to the two terminals. A reception unit has two terminals having a polar character and is configured to receive the ultrasonic wave transmitted from the transmission unit and to output a reception signal from the two terminals in accordance with the received ultrasonic wave. A change unit is configured to change a determination scheme for determining a type of a recording medium, based on information indicating a relation between a polar character of the transmission unit and a polar character of the reception unit, the information having been acquired from the reception signal.

Further features of the present invention will become apparent from the following description of exemplary embodiments (with reference to the attached drawings).

BRIEF DESCRIPTION OF THE DRAWINGS

FIG. 3 is a diagram for describing a drive signal, a reception signal, and a detection signal.

FIG. 8 is a diagram for describing the relation between a grammage and a transmission coefficient.

DESCRIPTION OF THE EMBODIMENTS

First Embodiment

Figure 1:
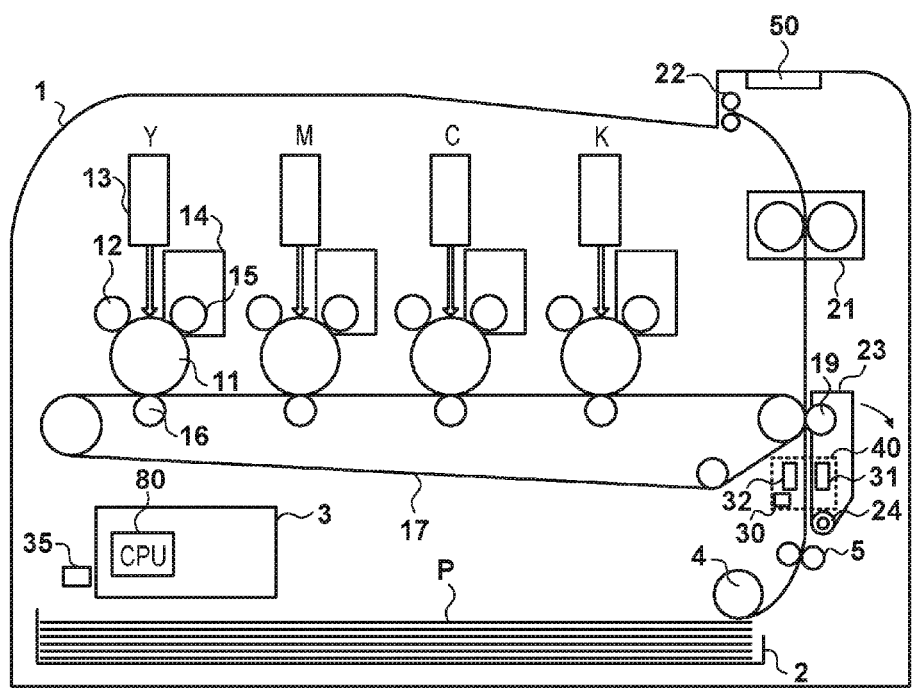
FIG. 1 is a schematic cross-sectional diagram of an image forming apparatus.

A grammage sensor according to the present embodiment can be used with an image forming apparatus such as a copier or a printer, for example. An image forming apparatus 1 equipped with the grammage sensor will be described with reference to FIG. 1. The image forming apparatus 1 is an image forming apparatus of a tandem type (four-drum system) in which an intermediate transfer belt 17 is adopted.

A feeding cassette 2 is a housing case for housing a recording medium P. An image forming control part 3 is a control part for controlling the image forming operations of the image forming apparatus 1. The image forming control part 3 is provided with a CPU 80, and sets image forming conditions based on a grammage acquired by a grammage sensor 40 and an environmental temperature acquired by an environment sensor 35. An operation part 50 has an input apparatus used by an operator for inputting information to the CPU 80 and a display apparatus used by the CPU 80 for displaying the information. A feeding roller 4 is a roller for feeding the recording medium P from the feeding cassette 2 to a conveyance path. A pair of conveying rollers 5 is for conveying the fed recording medium P.

The image forming apparatus 1 uses toner of four colors, which are yellow (Y), magenta (M), cyan (C), and black (K). Therefore, there are four image forming stations corresponding to the respective colors. Because the configuration is common among the respective stations, reference signs are only given to components that constitute the station for yellow.

A photoreceptor drum 11 is an image carrier that carries electrostatic latent images and toner images developed by a developing agent. A charging roller 12 is a primary charging device for uniformly charging the photoreceptor drum 11 to a predetermined potential. An optical unit 13 is an optical scanning apparatus (exposure apparatus) for irradiating the charged photoreceptor drum 11 with a laser beam corresponding to image data and forming an electrostatic latent image. A developing device 14 visualizes the electrostatic latent image formed on the photoreceptor drum 11 using the developing agent and forms the toner image. A developing roller 15 sends out the developing agent in the developing device 14 to a portion facing the photoreceptor drum 11. A primary transfer roller 16 is a roller for performing primary transfer of the toner image formed on the photoreceptor drum 11 to the intermediate transfer belt 17. The intermediate transfer belt 17 is an intermediate transfer body or an image carrier on which toner images of the four colors are superimposed and transferred. A secondary transfer roller 19 performs secondary transfer of the toner images formed on the intermediate transfer belt 17 to the recording medium P. A fixing unit 21 fuses and fixes the toner images transferred to the recording medium P while conveying the recording medium P. A paper discharge roller 22 discharges the recording medium P that underwent fixing by the fixing unit 21.

The grammage sensor 40 is one example of a recording medium determination apparatus for detecting the grammage information of the recording medium P. The grammage sensor 40 is arranged upstream of the secondary transfer roller 19 in a conveying direction. The grammage sensor 40 has a transmission part 31 for transmitting an ultrasonic wave, a reception part 32 for receiving the ultrasonic wave, and a sensor control part 30 for controlling these parts. The transmission part 31 and the reception part 32 are arranged to face each other with the conveyance path therebetween. The transmission part 31 is held, together with the secondary transfer roller 19, by a secondary transfer unit 23. The secondary transfer unit 23 opens and closes using a rotation shaft 24 as a fulcrum. In the case where the recording medium P which is being conveyed is jammed near the secondary transfer unit 23, a user can open the secondary transfer unit 23 and easily remove the jammed recording medium P. The CPU 80 determines the type (grammage) of the recording medium P based on a detection result of the grammage sensor 40. The grammage is the mass of the recording medium P per unit area. The grammage is expressed in units of $g/m^2$. Note that the CPU 80 may determine a thickness as the type of a recording medium based on the detection result. Moreover, the CPU 80 may determine multi-feeding of recording medium (a state where two or more stacked sheets of the recording medium P are simultaneously conveyed together) based on the detection result.

The CPU 80 performs control of image forming conditions during image forming in accordance with an output result obtained by the grammage sensor 40 and a detection result of the environment sensor 35 for detecting the environmental temperature. The image forming conditions include a conveying speed of the recording medium P, a transfer voltage applied to the secondary transfer roller 19, a fixing temperature of the fixing unit 21 and the like, for example.

The transmission part 31 and the reception part 32 may be constituted by identical components. The transmission part 31 and the reception part 32 have a piezoelectric element (also referred to as a piezo element) as a mutual transformation member for mutually transforming between a mechanical displacement (ultrasonic wave) and an electrical signal and two electrode terminals. In the transmission part 31, the piezoelectric element oscillates and an ultrasonic wave is generated when a pulse voltage of a predetermined frequency is applied as a drive signal to the two electrode terminals. The two terminals of the transmission part 31 are connected to two terminals of the piezoelectric element which also have a polar character. The two terminals of the reception part 32 are connected to two terminals of the piezoelectric element which also have a polar character. The ultrasonic wave is transmitted by the recording medium P and reaches the piezoelectric element of the reception part 32. However, the ultrasonic wave is attenuated by the recording medium P. The piezoelectric element of the reception part 32 generates an output voltage in accordance with the amplitude of the received ultrasonic wave, and outputs the output voltage from the two electrode terminals. The peak value of the amplitude of the output voltage (reception signal) varies in accordance with the type of the recording medium. This is because a transmission coefficient varies in accordance with the type of the recording medium. Note that sound waves other than ultrasonic waves may be used.

Figure 2:
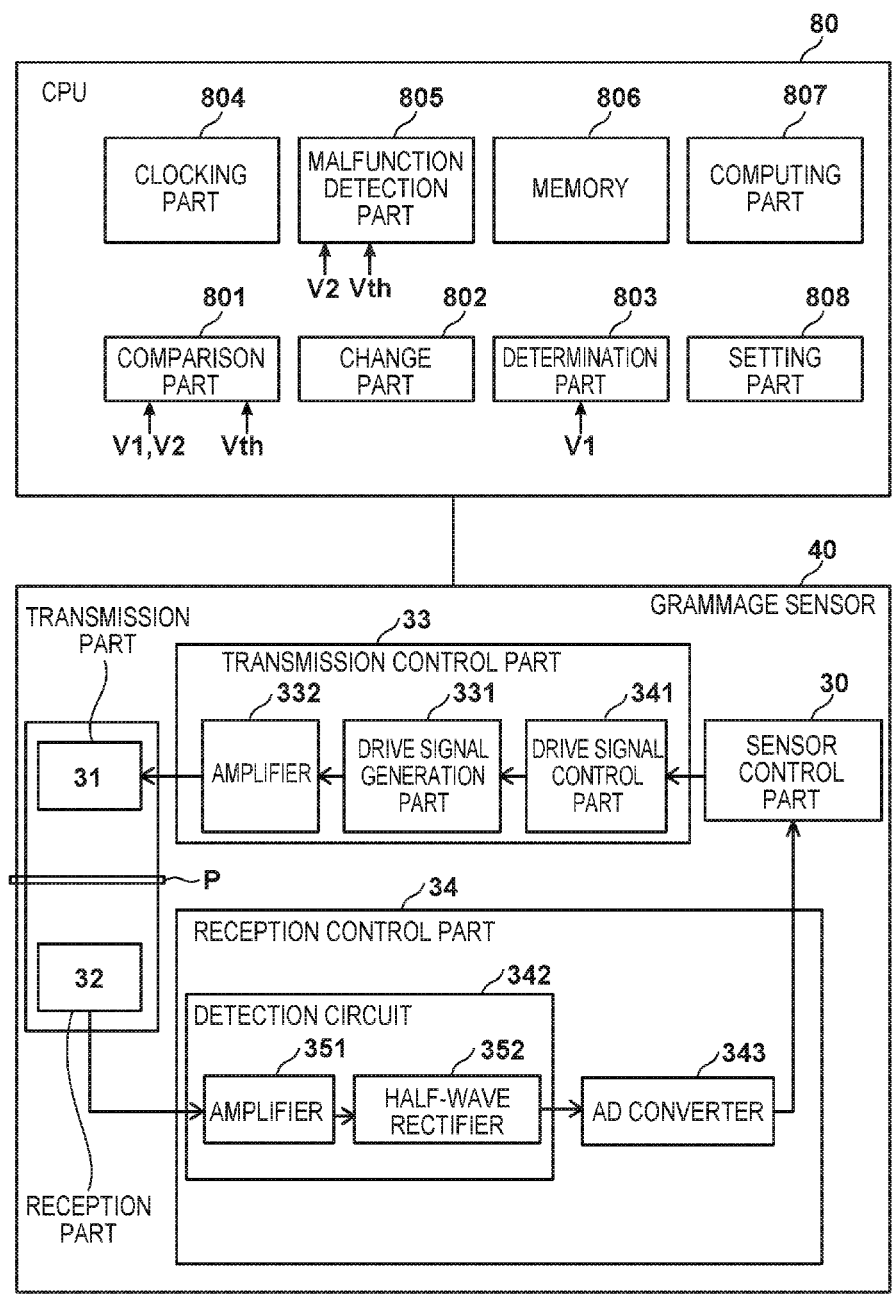
FIG. 2 is a block diagram of a grammage sensor.

A control method for detecting the grammage of the recording medium P using the grammage sensor 40 will be described with reference to FIG. 2. In the present embodiment, it is assumed that the transmission part 31 and the reception part 32 respectively transmits and receives an ultrasonic wave having a frequency response of 32 kHz. Although the frequency of the ultrasonic wave is set in advance, it is sufficient to appropriately select an appropriate frequency in accordance with the configurations of the transmission part 31 and the reception part 32, detection accuracy, and the like. The grammage sensor 40 is provided with a transmission control part 33 and a reception control part 34 in addition to the transmission part 31, the reception part 32, and the sensor control part 30. The transmission control part 33 has a function of generating a drive signal for transmitting the ultrasonic wave and amplifying the drive signal. The reception control part 34 has a function of amplifying the generated reception signal in accordance with the ultrasonic wave received by the reception part 32 and performing signal processing.

The sensor control part 30 inputs a start signal indicating measurement start to a drive signal control part 341. The drive signal control part 341 instructs the generation of the drive signal to a drive signal generation part 331 in order to transmit the ultrasonic wave of the predetermined frequency, when the start signal is input. The drive signal generation part 331 generates the drive signal in accordance with the instruction. In some cases, a reflection wave or the like is generated by the recording medium P or members around the conveyance path. Therefore, a pulse wave having a constant cycle shown in FIG. 3 is output as the drive signal in order to reduce the influence of such an external disturbance so that the reception part 32 can receive only direct waves irradiated by the transmission part 31. This is also called a burst wave in some cases. The transmission part 31 according to the present embodiment transmits 16 burst waves per measurement. The interval between two adjacent burst waves is 10 ms. Moreover, one burst is formed by consecutively outputting five pulse waves having a frequency of 32 kHz. The drive signal generation part 331 generates the drive signal having a preset frequency and outputs the drive signal. An amplifier 351 amplifies the level (voltage) of the drive signal, and outputs the drive signal to the transmission part 31.

The reception part 32 receives an ultrasonic wave transmitted from the transmission part 31, or an ultrasonic wave transmitted by the recording medium P, and outputs the received ultrasonic wave to a detection circuit 342 of the reception control part 34. The detection circuit 342 is provided with the amplifier 351 and a half-wave rectifier 352. The amplifier 351 amplifies the reception signal output by the reception part 32. The half-wave rectifier 352 performs half-wave rectification on the amplified reception signal. Note that the amplification factor of the amplifier 351 may be changed between the state where the recording medium P does not exist between the transmission part 31 and the reception part 32 and the state where the recording medium P does exist.

FIG. 3 shows the waveform of the reception signal output by the reception part 32. Potentials indicated by broken lines as shown in FIG. 3 are ground potentials. As shown in FIG. 3, the reception signal has a waveform with amplitudes of both positive and negative polar characters. Furthermore, FIG. 3 also illustrates the waveform of the reception signal after the half-wave rectification. As for this waveform, a potential indicated by a broken line also represents a ground potential. A detection signal generated by the detection circuit 342 based on the reception signal is converted from an analogue signal into a digital signal by an AD converter 343, and is input to the sensor control part 30. Note that the detection signal is generated based on the reception signal and therefore may be called a reception signal.

The CPU 80 realizes various functions. A comparison part 801 compares a polar character parameter with a threshold. The polar character parameter is information indicating the relation between the polar character of the transmission part 31 for transmitting an ultrasonic wave and the polar character of the reception part 32 for receiving the ultrasonic wave. A change part 802 changes a determination scheme for determining the type of the recording medium P based on the comparison result of the comparison part 801. A determination part 803 determines the type of the recording medium P using the determination scheme which has been set or designated by the change part 802. A setting part 808 sets the image forming conditions based on the determination result of the determination part 803. Moreover, the setting part 808 may set the image forming conditions directly from the value of the reception signal. A measuring part 804 is a timer or a counter, and is used for managing various types of timings. A malfunction detection part 805 detects a malfunction of the transmission part 31 or the reception part 32. A memory 806 stores thresholds, tables, flags and the like. A computing part 807 executes various types of computing using the environmental temperature acquired by the environment sensor 35, for example.

The waveform of the reception signal shown in FIG. 3 is a waveform in the case where the recording medium P does not exist between the transmission part 31 and the reception part 32. Generally, a speed of sound v propagated through air is obtained from the following formula.

$$V = 331.5 + 0.61 * t$$

(t is the temperature in Celsius)

If it is assumed that a distance d between the transmission part 31 and the reception part 32 is 10 mm and that the environmental temperature is 20 C, a sound wave propagation time $\Delta t1$ will be 29.095 μs. As one example of a grammage determination method, there is a method for determining a grammage based on the amplitude (voltage V1) of a detection signal detected at a timing D when a certain period of time ($1/4*T+\Delta t1$) has elapsed from a timing when the transmission control part 33 generated a third pulse wave. Note that T is a cycle of the drive signal (pulse wave).

The CPU 80 or the sensor control part 30 causes the grammage sensor 40 to respectively detect the voltages V1 in a state where the recording medium P does not exist between the transmission part 31 and the reception part 32 and in a state where the recording medium P does exist. The CPU 80 then individually calculates transmission coefficients c from the voltages V1 obtained in the two states. The transmission coefficient c is a value corresponding to the grammage calculated from the comparison of the voltages V1 in the state where the recording medium P does not exist and in the state where the recording medium P does exist in this manner, and is used for determining the grammage of the recording medium P.

Figure 4A:
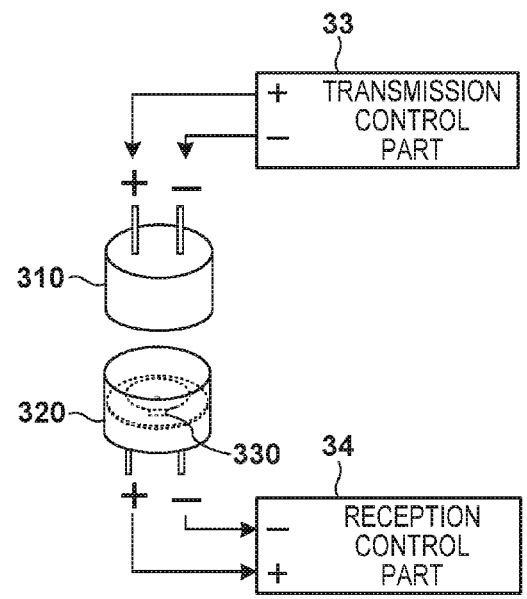
FIGS. 4A to 4F are diagrams for describing the difference of signal waveforms due to the difference of polar characters.
Figure 4B:
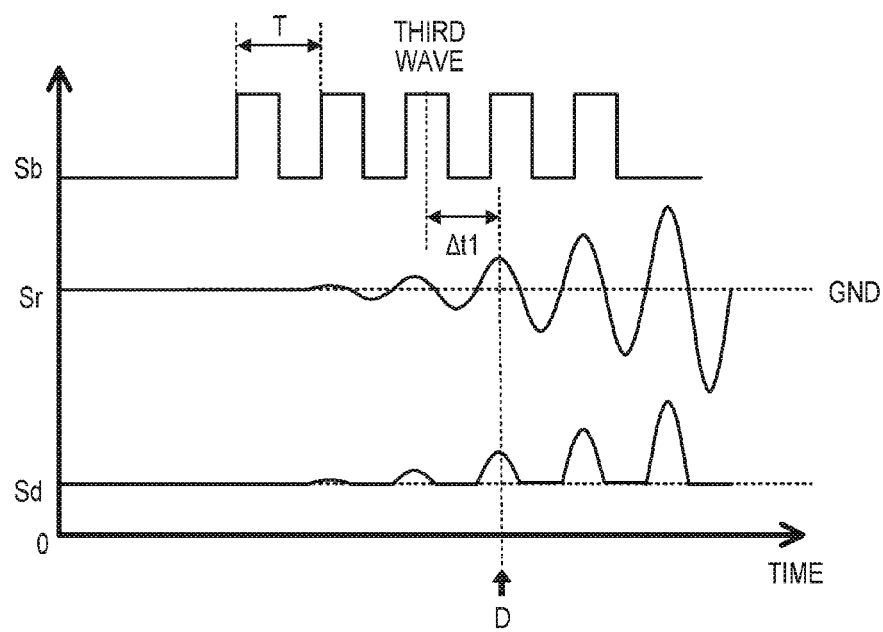
Figure 4C:
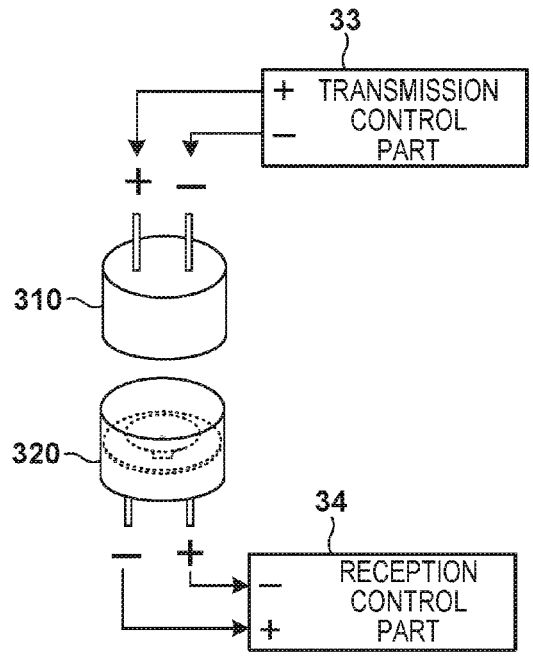
Figure 4D:
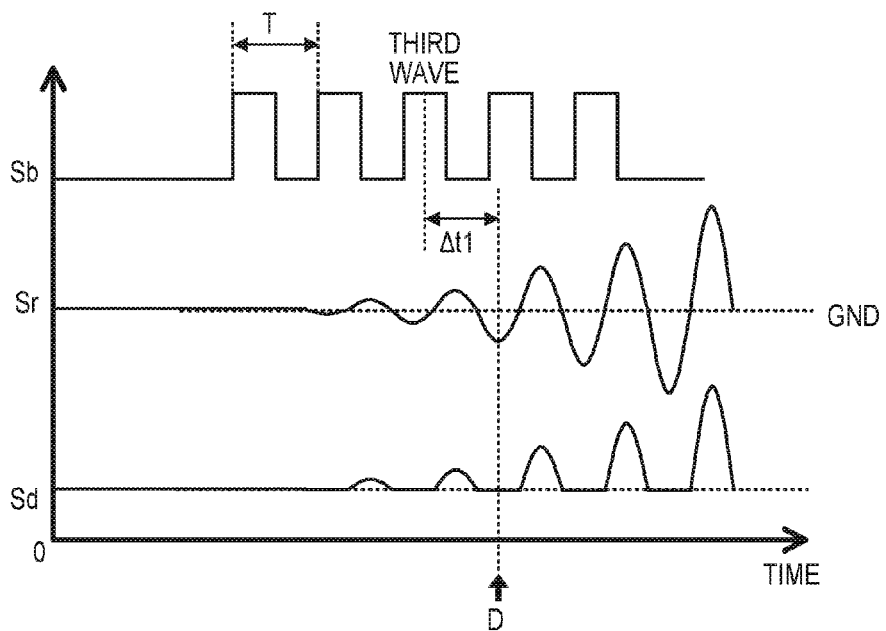
Figure 4E:
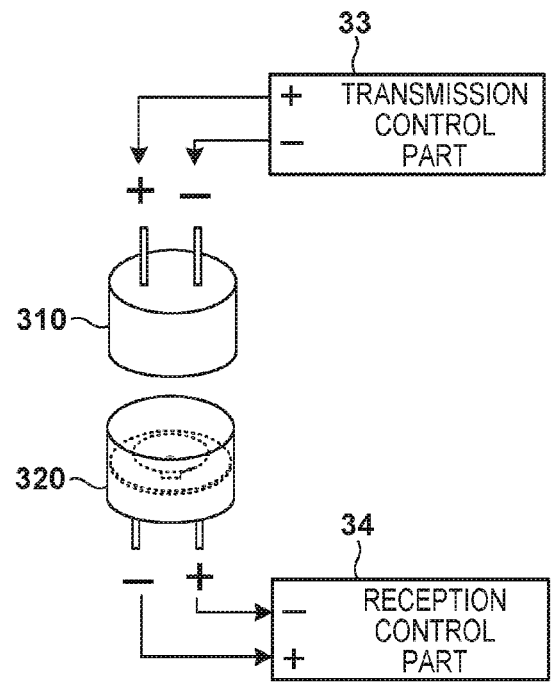
Figure 4F:
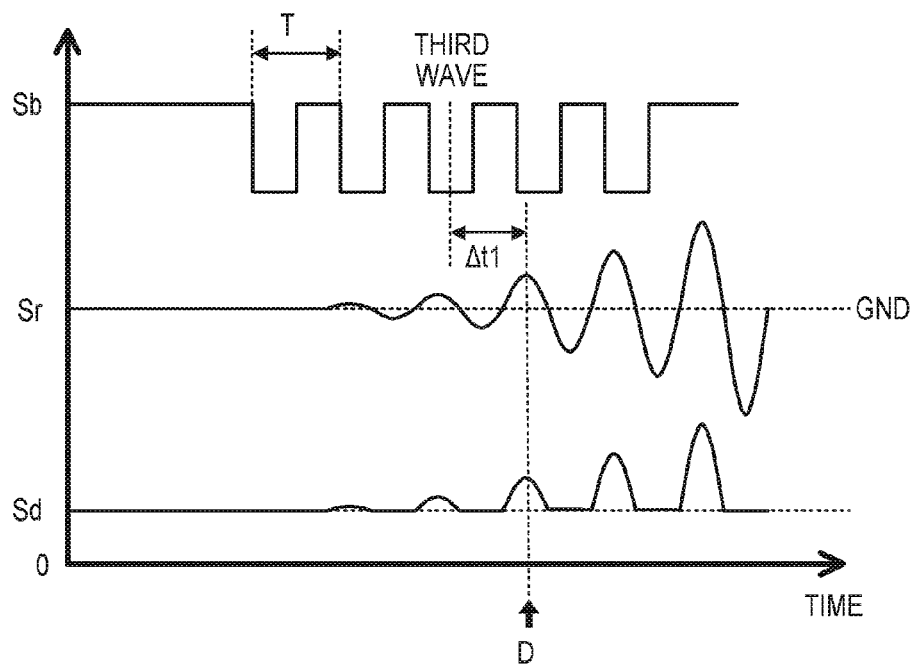

The polar characters of the ultrasonic wave sensors equipped in the transmission part 31 and the reception part 32 will be described with reference to FIG. 4A to FIG. 4F. Polar characters exist in a piezoelectric element 330 constituting the ultrasonic wave sensor. FIG. 4A, FIG. 4C and FIG. 4E show the terminal polar characters of the ultrasonic wave sensor and a connection state between the polar characters of the transmission control part 33 and the reception control part 34. FIG. 4B, FIG. 4D and FIG. 4F indicate waveforms of a drive signal, a reception signal, and a detection signal.

With reference to FIG. 4A, a positive polar character output and a negative polar character output of the transmission control part 33 are respectively connected to a positive polar character terminal and a negative polar character terminal of an ultrasonic wave sensor 310 included in the transmission part 31. A positive polar character input and a negative polar character input of the reception control part 34 are respectively connected to a positive polar character terminal and a negative polar character terminal of an ultrasonic wave sensor 320 included in the reception part 32. Such a connection state is expressed as "polar characters match". With reference to FIG. 4B, when a drive signal Sb, which is a burst wave, is applied to the ultrasonic wave sensor 310, a reception signal Sr is generated in the ultrasonic wave sensor 320, and a detection signal Sd is generated by the reception control part 34. Note that the drive signal Sb is started at a high level, and therefore the amplitude of the reception signal Sr starts with a positive amplitude. The amplitude (voltage) of the detection signal Sd is acquired at the timing D.

With reference to FIG. 4C, the positive polar character output and the negative polar character output of the transmission control part 33 are respectively connected to the positive polar character terminal and the negative polar character terminal of the ultrasonic wave sensor 310 on the transmission side. The negative polar character input and the positive polar character input of the reception control part 34 are respectively connected to the positive polar character terminal and the negative polar character terminal of the ultrasonic wave sensor 320 on the reception side. As shown in FIG. 4D, when the drive signal Sb that is started at a high level is applied to the ultrasonic wave sensor 310, the amplitude of the reception signal Sr starts with a negative amplitude. As a result, the amplitude of the detection signal Sd at the timing D substantially becomes a ground potential. Such a connection state is expressed as "polar characters do not match".

In this manner, the amplitude of the detection signal Sd at the timing D when the polar characters of the ultrasonic wave sensor 310 and the ultrasonic wave sensor 320 match does not coincide with the amplitude of the detection signal Sd at the timing D when the polar characters do not match. For example, if the connection state of FIG. 4A is assumed to be a basic connection state, the connection state of FIG. 4C and FIG. 4E can be called a reverse connection state. Moreover, these connection states can be distinguished using the amplitude of the detection signal Sd at the timing D when a predetermined time has elapsed from a timing when transmission of the drive signal Sb was started. That is, it can be said that the amplitude of the detection signal Sd at the timing D is a polar character parameter or a feature parameter indicating the feature of the connection state (polar character) between the transmission part 31 and the reception part 32. Accordingly, it is sufficient to select a method for determining the type of the recording medium P in accordance with the polar character parameter if it is known. Note that the determination method here includes control of a starting amplitude of the drive signal Sb.

The sensor control part 30 or the change part 802 of the CPU 80 changes the drive signal Sb to the drive signal Sb shown in FIG. 4F when the reverse connection state is detected based on the amplitude of the detection signal Sd at the timing D. The amplitude of the drive signal Sb shown in FIG. 4F is started at a low level. The amplitude of the detection signal Sd acquired at the timing D as shown in FIG. 4F will match the amplitude of the detection signal Sd in a basic connection state as shown in FIG. 4B.

Description was given with reference to FIG. 4A to FIG. 4F in which all of the connection states regarding the transmission side of the ultrasonic wave sensor 310 are in common. However, the connection states regarding the reception side of the ultrasonic wave sensor 320 may be in common and the connection states regarding the transmission side of the ultrasonic wave sensor 310 may be different. Also in this case, it is sufficient that the amplitude of the drive signal Sb starts at a high level if the amplitude of the detection signal Sd at the timing D is a positive amplitude and that the amplitude of the drive signal Sb starts at a low level if the amplitude of the detection signal Sd at the timing D is a ground potential. In this manner, it is sufficient that the method for determining the type of a recording medium is selected or changed in accordance with the amplitude of the detection signal Sd acquired at the timing D (a starting amplitude of the drive signal Sb), which is a polar character parameter.

Figure 5A:
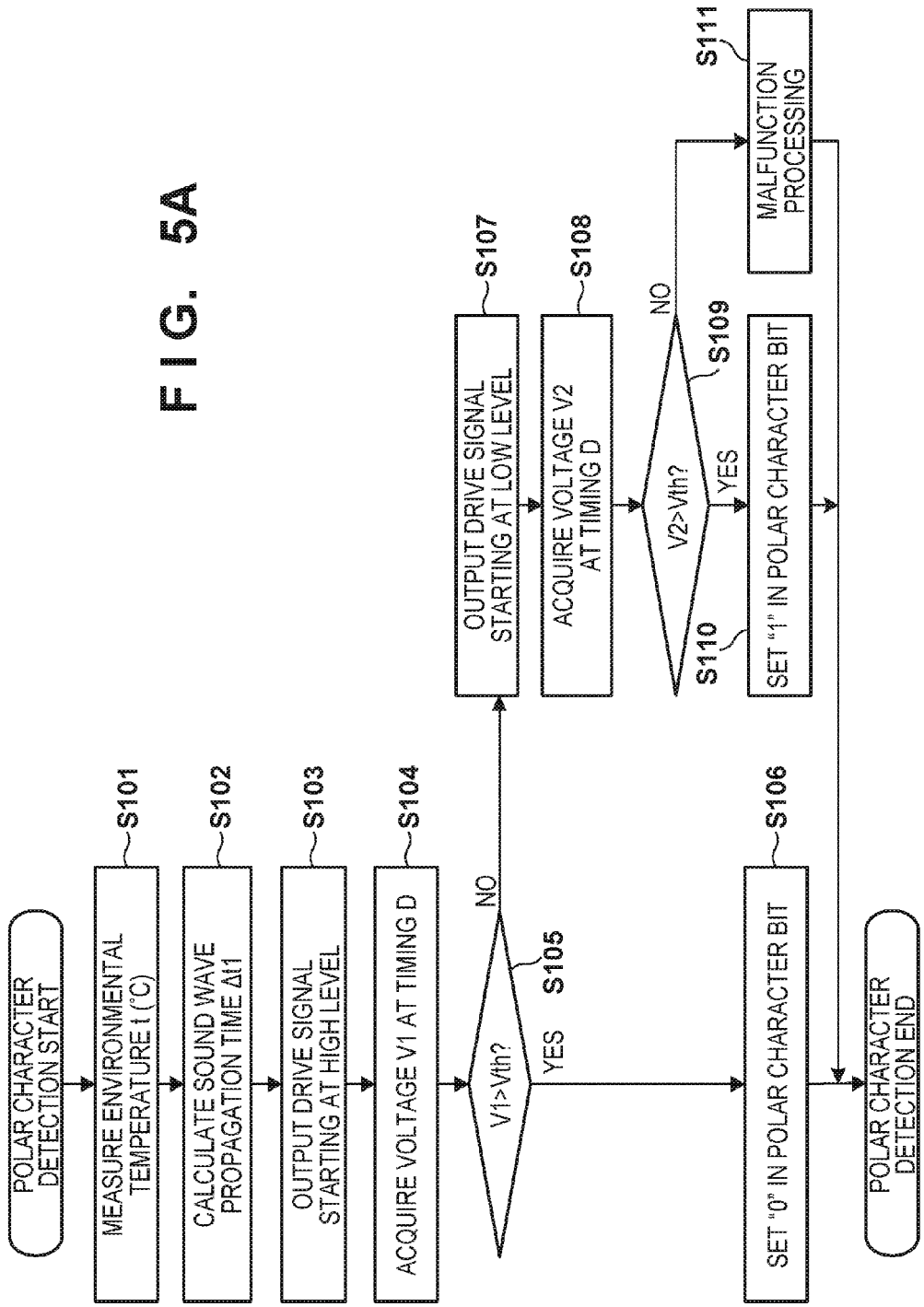
FIGS. 5A and 5B are respectively a flowchart showing processing for detecting the polar character of an ultrasonic wave sensor and a flowchart showing processing for detecting the type of a recording medium.

A polar character (connection state) detection method will be described with reference to a flowchart in FIG. 5A. The CPU 80 controls the sensor control part 30 by executing a program stored in the CPU 80. Moreover, the sensor control part 30 controls each part of the grammage sensor 40. Note that the polar character detection method is executed when the supply of electrical power from an alternating current power to the image forming apparatus 1 is started.

In step S101, the computing part 807 of the CPU 80 measures, using the environment sensor 35, a temperature t of the surrounding environment in which the image forming apparatus 1 is placed. In step S102, the computing part 807 of the CPU 80 calculates a sound wave propagation time $\Delta t1$ [seconds] based on the measured temperature t.

$\Delta t1 = d/v$ d is a distance [m] between the vibration surface of the piezoelectric element of the transmission part 31 and the vibration surface of the piezoelectric element of the reception part 32. For example, d is 0.01 m. v is a propagation speed of an ultrasonic wave [m/s] at the temperature t (v=331.5+0.6t).

In step S103, the change part 802 of the CPU 80 instructs the sensor control part 30 to output a drive signal Sb that starts at a high level. The sensor control part 30 instructs the drive signal control part 341 of the transmission control part 33 to output the drive signal Sb that starts at a high level in accordance with this instruction. The drive signal control part 341 instructs the drive signal generation part 331 to output the drive signal Sb that starts at a high level. The drive signal generation part 331 starts output of the drive signal Sb that starts at a high level.

In step S104, the CPU 80 controls the sensor control part 30 and obtains the amplitude of a detection signal Sd (a voltage V1) from the reception control part 34 after a predetermined time from a timing when transmission of an ultrasonic wave based on the drive signal Sb was started. The timing when the predetermined time has elapsed is the above-described timing D, and is a timing when $1/4*T+\Delta t1$ has elapsed from a timing when a third pulse wave was output. That is, the timing D using the timing when transmission of an ultrasonic wave was started as a starting point is a timing when a time of $2T+1/4*T+\Delta t1$ has elapsed from a timing when a first pulse wave was output. In this case, the predetermined time is $2T+1/4*T+\Delta t1$. The sensor control part 30 transmits the voltage V1 to the CPU 80. Note that the CPU 80 uses the measuring part 804 to measure and monitor each timing.

In step S105, the comparison part 801 of the CPU 80 determines whether or not the voltage V1 exceeds a predetermined threshold Vth. The threshold Vth is a voltage that serves as a criterion for determining whether or not polar characters match, is set in advance at the time of shipping, and is stored in the memory 806 inside the CPU 80 or the like. As described with reference to FIG. 4B, if the voltage V1 exceeds the predetermined threshold Vth, the polar characters of the transmission part 31 and the reception part 32 match. Accordingly, in this case, the process proceeds to step S106, and the CPU 80 sets "0" in a polar character bit. The polar character bit is a flag or data for managing whether or not the polar characters match. Moreover, the polar character bit is also data designating a method for determining the type of the recording medium P. "0" indicates that the polar characters match and "1" indicates that the polar characters do not match. The polar character bit is stored in a rewritable ROM included in the memory 806, for example. On the other hand, if the voltage V1 does not exceed the predetermined value Vth, the polar characters do not match, and therefore the process proceeds to step S107.

In step S107, the change part 802 of the CPU 80 instructs to start output of the drive signal Sb that starts at a low level. This instruction is communicated via the sensor control part 30 and the drive signal control part 341 to the drive signal generation part 331. The drive signal generation part 331 starts generation of the drive signal Sb that starts at a low level in accordance with the instruction. The drive signal Sb that starts at a low level is shown in FIG. 4F.

In step S108, the CPU 80 acquires a voltage V2 at the timing D. In step S109, the comparison part 801 of the CPU 80 determines whether or not the voltage V2 exceeds the threshold Vth. If the voltage V2 exceeds the threshold Vth, the polar characters match, and therefore the process proceeds to step S110. In step S110, the change part 802 of the CPU 80 writes "1" in the polar character bit. Note that in the case where the malfunction detection part 805 detects that the voltage V2 does not exceed the threshold Vth, it is possible that a malfunction has occurred somewhere in the grammage sensor 40 such as the transmission part 31 or the reception part 32. In this case, the process proceeds to step S111, and the malfunction detection part 805 of the CPU 80 executes malfunction processing. The malfunction processing involves the CPU 80 displaying, on a display unit, a message informing the malfunction of the grammage sensor 40, or transmitting an e-mail informing this malfunction to the address of an administrator.

Figure 5B:
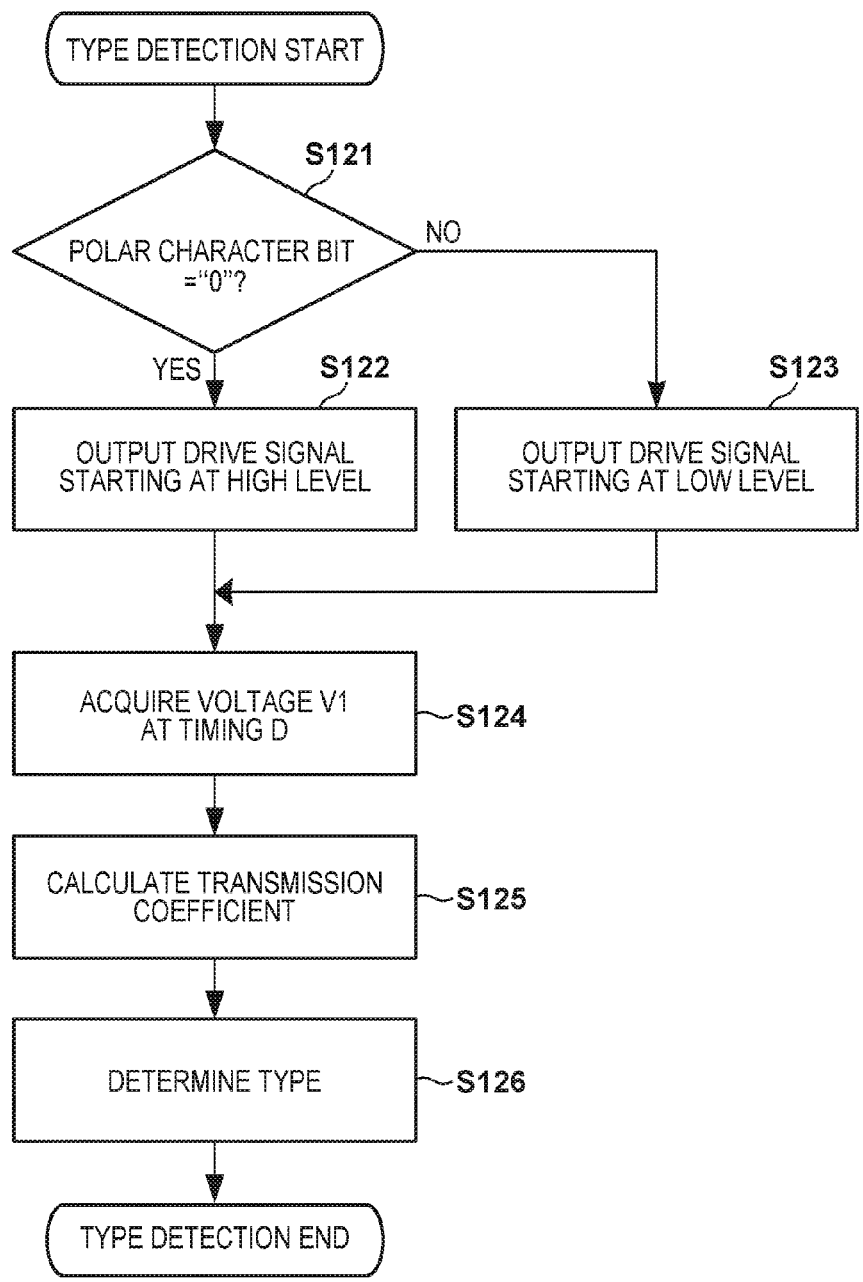

FIG. 5B shows type determination processing. The type determination processing is executed when the recording medium P is fed from the feeding cassette 2. In step S121, the change part 802 of the CPU 80 refers to the polar character bit, and determines whether or not "0" is set in the polar character bit. If "0" is set in the polar character bit, the process proceeds to step S122. In step S122, the change part 802 instructs the sensor control part 30 to output a drive signal that starts at a high level. On the other hand, if "0" is not set in the polar character bit, the process proceeds to step S123. In step S123, the change part 802 instructs the sensor control part 30 to output a drive signal that starts at a low level. Subsequently, the process proceeds to step S124. Note that an output start timing of the drive signal Sb is a timing when the recording medium P passes between the transmission part 31 and the reception part 32.

In step S124, the determination part 803 of the CPU 80 acquires a voltage V1 at the timing D. In step S125, the determination part 803 calculates the transmission coefficient c based on the voltage V1. Note that a voltage V0 acquired in advance at a timing when the recording medium P was not passing between the transmission part 31 and the reception part 32 is also used (e.g., c=V1/V0) when calculating the transmission coefficient c.

In step S126, the determination part 803 determines the type (grammage) of the recording medium P based on the transmission coefficient c. Note that the relation between the transmission coefficient c and the type (grammage) of the recording medium P is held in advance in the memory 806 or the like as a function or a table. The determination part 803 calculates the grammage by substituting the transmission coefficient c into the function, or determines the grammage by referring to the table based on the transmission coefficient c. The setting part 808 sets an image forming condition in accordance with the type of the recording medium P. The relation between the type of the recording medium P and the image forming condition may be stored in the memory 806 as a table or a function.

Note that the present embodiment described polar character detection being executed when starting the image forming apparatus 1, but the execution timing of the polar character detection may be another timing. This is because it is sufficient that the polar character detection is executed at least before executing the type determination processing. For example, the CPU 80 may execute the polar character detection at the time of shipping the image forming apparatus 1 and the store polar character bits in a nonvolatile memory in the memory 806. However, in the market, when a component that constitutes the grammage sensor 40 is replaced, a user or a serviceman will cause the CPU 80 to execute polar character detection through the operation part 50 provided on the image forming apparatus 1.

According to the present embodiment, the polar character parameter is acquired from the reception signal of the ultrasonic wave, and the determination scheme for the recording medium is changed in accordance with the polar character parameter. In particular, in the present embodiment, the voltage of the detection signal Sd at the timing D was illustrated as the polar character parameter. Accordingly, because the necessity of managing each polar character of the transmission part 31 and the reception part 32 of the ultrasonic wave while assembling the components during manufacture is eliminated, the cost of the recording medium determination apparatus can be reduced.

Second Embodiment

In the first embodiment, the voltage of the detection signal Sd at the timing D was illustrated as the polar character parameter. In the second embodiment, a fall time tdown of a zero cross signal Se obtained from the reception signal Sr will be illustrated as a polar character parameter.

Figure 6:
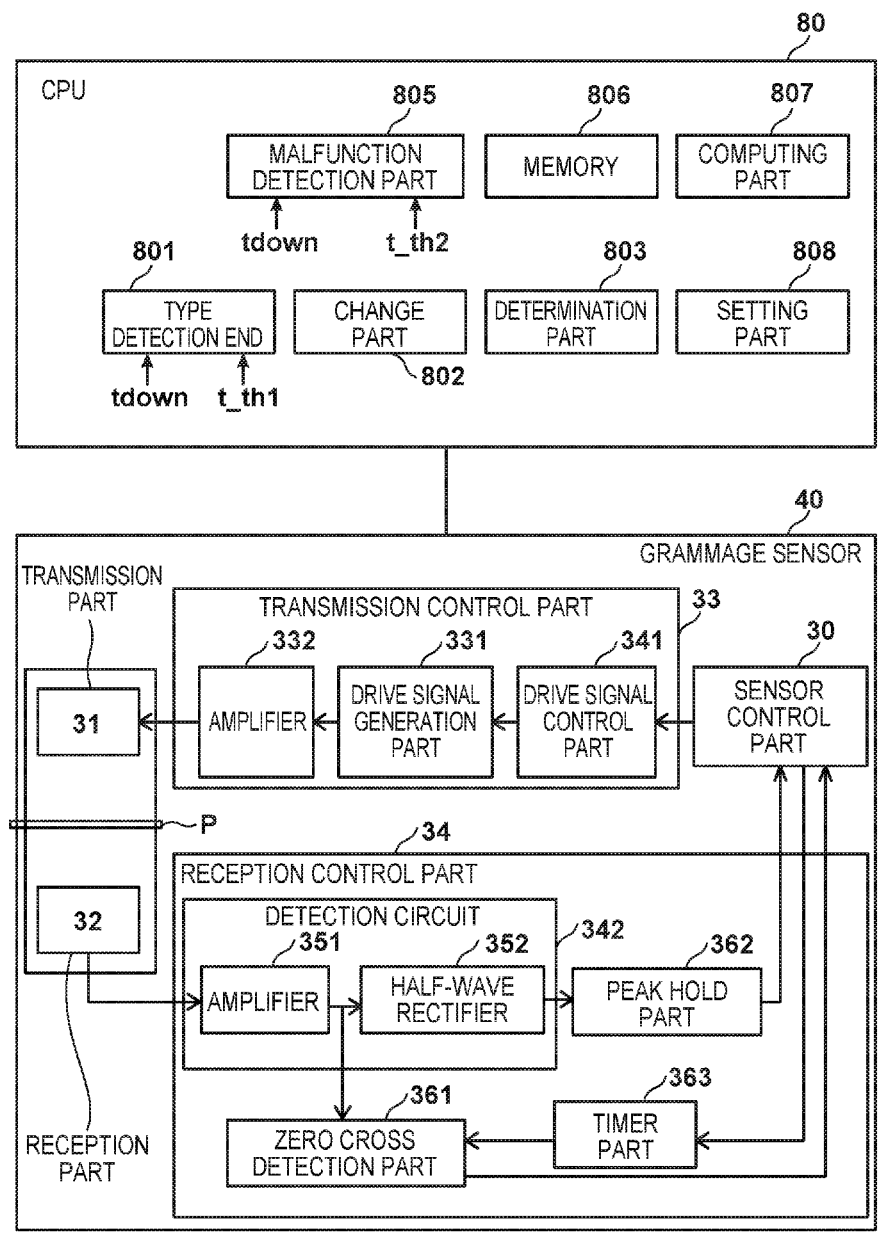
FIG. 6 is a block diagram of a grammage sensor.

FIG. 6 is a circuit block diagram of the present embodiment. In FIG. 6, a difference from FIG. 2 is the reception control part 34, in particular. Specifically, a peak hold part 362, a zero cross detection part 361, and a timer part 363 are added. Note that, in FIG. 6, same reference signs are given to the functions that are the same as those in FIG. 2 and description thereof is omitted. A reception signal generated by receiving an ultrasonic wave in the reception part 32 is subjected to amplification and half-wave rectification in the detection circuit 342 and becomes a detection signal. The peak hold part 362 connected to the detection circuit 342 holds the peak voltage of the detection signal, and outputs the peak voltage to the sensor control part 30.

The reception signal amplified by the amplifier 351 is also input to the zero cross detection part 361. The zero cross detection part 361 compares the input reception signal to a threshold (e.g., a ground potential). The zero cross detection part 361 outputs a high level signal if the reception signal is greater than or equal to a ground potential, and outputs a low level signal if the reception signal is smaller than the ground potential. In this manner, the signal output from the zero cross detection part 361 becomes a pulse signal whose level changes at the zero cross point of the reception signal. A gate mask is applied to the output of the zero cross detection part 361 by a control signal Si output from the timer part 363. The timer part 363 starts measuring based on an instruction from the sensor control part 30. For example, the sensor control part 30 instructs the measuring in synchronization with a transmission start timing of the ultrasonic wave. The zero cross detection part 361 is provided with a switch element (e.g., a transistor or the like), and controls whether or not to output the signal to the sensor control part 30 using this switch element. The control signal Si from the timer part 363 is applied to a control terminal of the switch element. The timer part 363 masks (blocks outputting of) the output signal from the zero cross detection part 361 until a predetermined time Tg elapses from a measuring start timing. When the predetermined time Tg elapses, the level of the control signal Si from the timer part 363 changes, and the switch element outputs the output signal from the zero cross detection part 361 to the sensor control part 30. Such a function of the switch element may be called gate mask.

The CPU 80 realizes various functions. The comparison part 801 compares a polar character parameter (e.g., the fall time tdown) and a threshold (e.g., t_th1). The change part 802 changes the determination scheme for determining the type of the recording medium P based on the comparison result of the comparison part 801. The determination part 803 determines the type of the recording medium P using the determination scheme set or designated by the change part 802. The setting part 808 sets image forming conditions in accordance with the determination result of the determination part 803. The malfunction detection part 805 detects a malfunction of the transmission part 31 or the reception part 32. The memory 806 stores thresholds, tables, flags and the like. The computing part 807 executes various types of computing using an environmental temperature obtained by the environment sensor 35, for example.

Figure 7A:
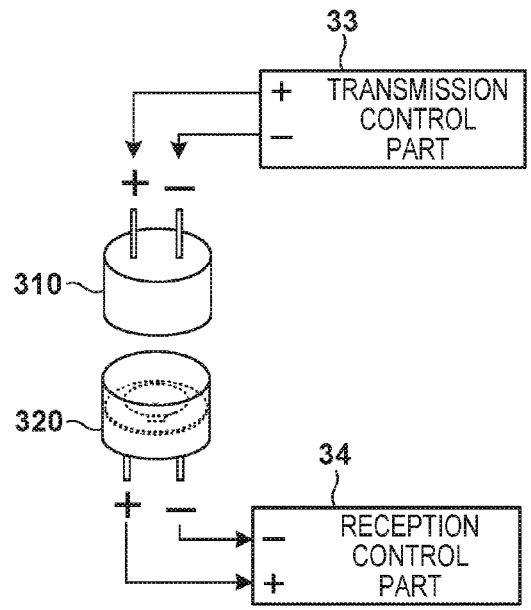
FIGS. 7A to 7D are diagrams for describing the difference of signal waveforms due to the difference of polar characters.
Figure 7B:
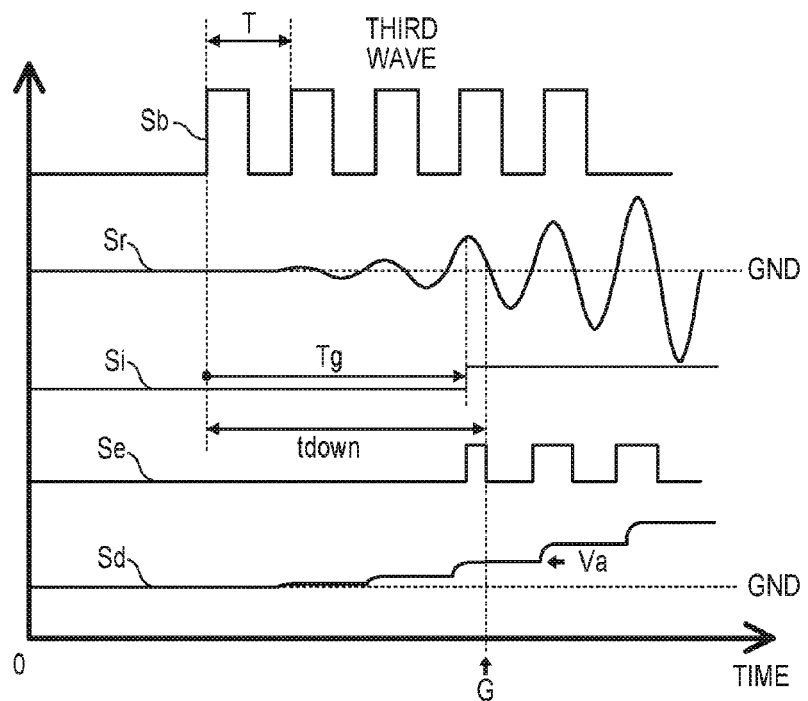

FIG. 7A shows a connection state where the polar characters of the ultrasonic wave sensor 310 on the transmission side and the ultrasonic wave sensor 320 on the reception side match (basic connection state). FIG. 7B shows waveforms of the respective signals in the basic connection state. Note that the same reference signs are given to the portions that have already been described and description thereof is omitted. The drive signal Sb and the reception signal Sr are as described above. Si is a control signal output by the timer part 363. Se is a zero cross signal output from the zero cross detection part 361 to the sensor control part 30. A gate mask has been applied to the zero cross signal Se by the control signal Si as described above. Therefore, during the period in which the signal Si is at a low level, the zero cross signal Se is also at a low level. On the other hand, during the period in which the control signal Si is at a high level, the zero cross signal Se is a pulse wave in accordance with the zero cross of the reception signal Sr.

A timing for changing the control signal Si from the low level to the high level is a timing when the predetermined time Tg has elapsed from an output start timing of the drive signal Sb. The predetermined time Tg is calculated by the computing part 807 based on a sound wave propagation time calculated from a distance between the transmission part 31 and the reception part 32 and an environmental temperature. Here, the predetermined time Tg is set to a time from a transmission start timing of the drive signal Sb until a timing when the peak voltage of the third wave of the reception signal Sr is obtained (Tg=2T+1/4T+Δt).

The detection signal Sd is a signal obtained by the peak hold part 362 holding the peak of the reception signal Sr. The sensor control part 30 reads a voltage Va of the detection signal Sd at a timing G when a first falling edge of the zero cross signal Se serves as a trigger. In grammage detection, the voltage Va when the recording medium P does not exist between the transmission part 31 and the reception part 32 and the voltage Va when the recording medium P does exist are individually detected, and the difference or the ratio thereof is calculated as a transmission coefficient. Moreover, a grammage is determined from the transmission coefficient by referring to a table indicating the relation between the transmission coefficient, which is obtained in advance, and the grammage.

Figure 7C:
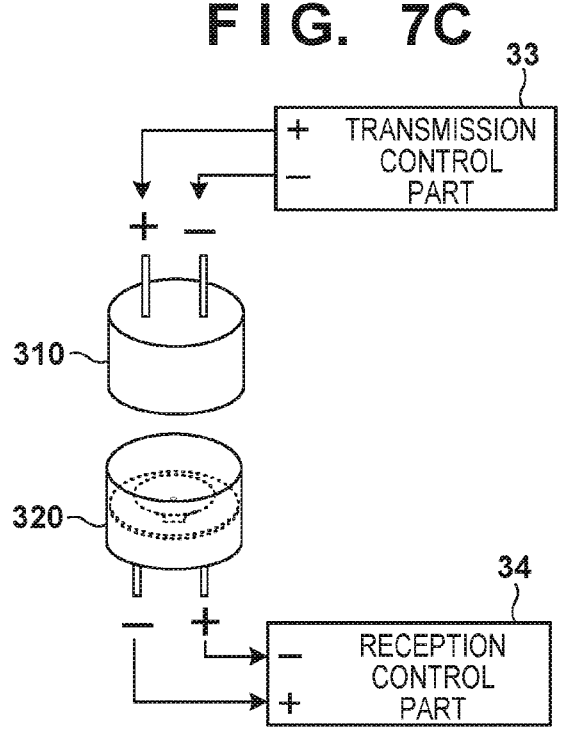
Figure 7D:
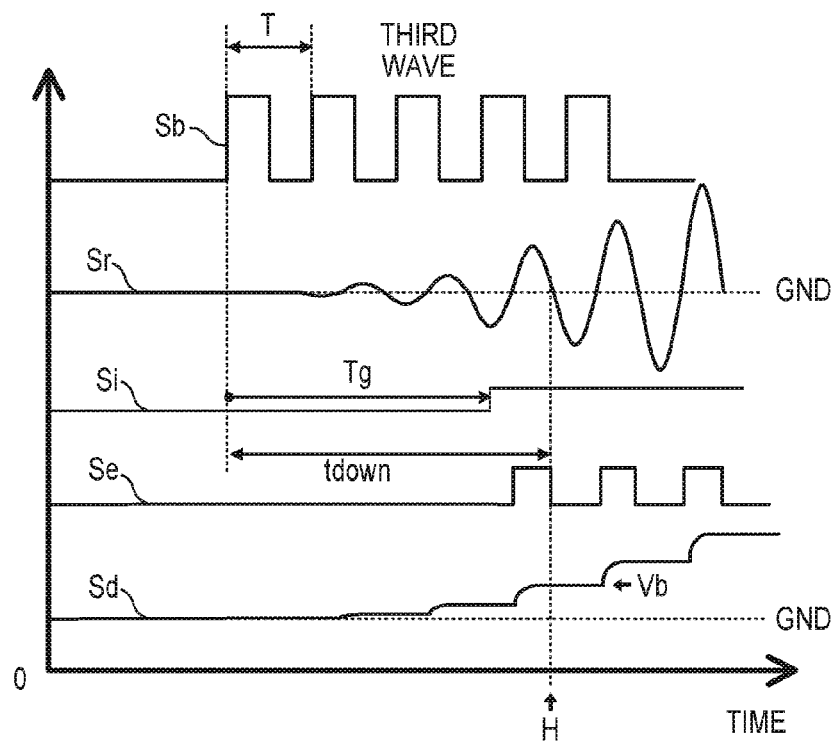

FIG. 7C shows a connection state where the polar characters of the ultrasonic wave sensor 310 on the transmission side and the ultrasonic wave sensor 320 on the reception side do not match (reverse connection state). FIG. 7D shows waveforms of the respective signals in the reverse connection state. Comparing FIG. 7D with FIG. 7B, the amplitude of the reception signal Sr in the reverse connection state is the inverse of the amplitude of the reception signal Sr in the basic connection state. A voltage Vb read by the sensor control part 30 at a timing H when the zero cross signal Se serves as a trigger becomes a voltage corresponding to a center point between a third wave and a fourth wave (Vb>Va). Note that the predetermined time Tg is set to a time from a transmission start timing of the drive signal Sb until a timing when the peak voltage of the center point between the third wave and the fourth wave of the reception signal Sr is obtained (Tg=2.5T+1/4T+Δt).

FIG. 8 shows respective transmission coefficients for the voltage Va acquired at the timing G corresponding to the third wave of the drive signal Sb and for the voltage Vb acquired at the timing H corresponding to the center point between the third wave and the fourth wave. As shown in FIG. 8, the transmission coefficient varies in accordance with the connection state even for the recording medium P of the same grammage (e.g., 105 g/m$^2$). Therefore, grammage determination tables need to be switched in accordance with the connection state. The memory 806 of the CPU 80 stores a table A for the basic connection state and a table B for the reverse connection state in advance.

In order to determine which table is to be used by the CPU 80 for grammage determination, a connection state (polar character) between the ultrasonic wave sensor 310 of the transmission part 31 and the ultrasonic wave sensor 320 of the reception part 32 needs to be detected. For example, the CPU 80 detects the time tdown from the transmission start timing of the drive signal Sb until a first falling timing of the zero cross signal Se. In the case where the time tdown is smaller than the predetermined time t_th1, the CPU 80 determines that the connection state is the basic connection state and uses the table A for the basic connection state. On the other hand, in the case where the time tdown is greater than or equal to t_th1, the CPU 80 determines that the connection state is the reverse connection state, and uses the table B for the reverse connection state.

Figure 9:
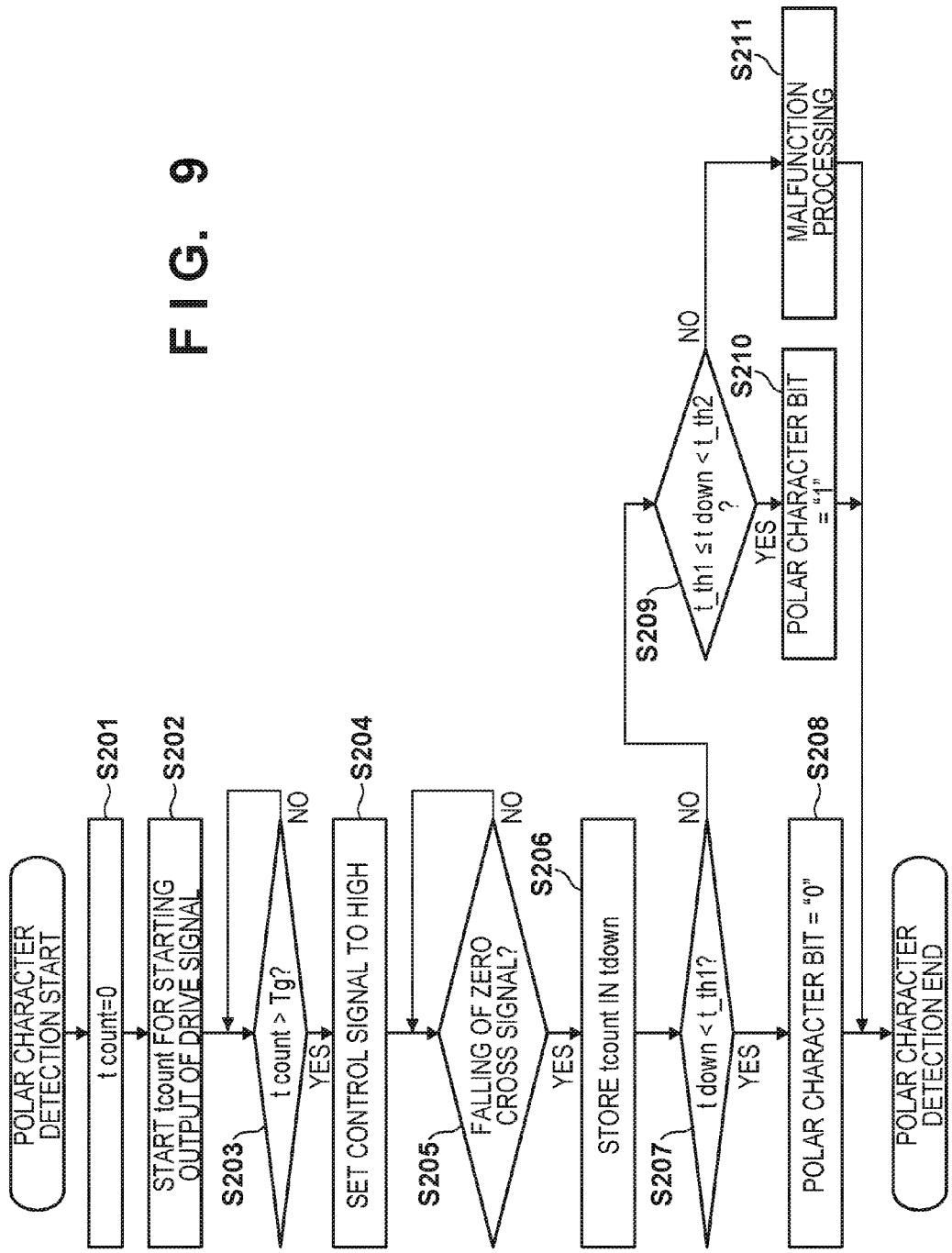
FIG. 9 is a flowchart showing processing for detecting the polar character of an ultrasonic wave sensor.

FIG. 9 is a flowchart showing each step of a polar character detection method executed by the CPU 80. This polar character detection method is executed when starting the image forming apparatus 1, for example. In step S201, the CPU 80 initializes the timer part 363 for measuring time through the sensor control part 30 (tcount=0). In step S202, the CPU 80 starts outputting of the drive signal through the sensor control part 30, and causes the timer part 363 to start counting. In step S203, the CPU 80 determines whether or not the count value tcount of the timer part 363 has exceeded the predetermined time Tg. When the count value tcount exceeds the predetermined time Tg, the process proceeds to step S204. Note that the predetermined time Tg may be calculated by the computing part 807, or may be a fixed value stored in the memory 806. In step S204, the CPU 80 changes a gate mask signal (the control signal Si) output by the timer part 363 from a low level to a high level. In step S205, the CPU 80 monitors the zero cross signal Se, and determines whether or not the falling edge of the zero cross signal Se has been detected. When the falling edge of the zero cross signal Se is detected, the process proceeds to step S206. In step S206, the CPU 80 acquires, from the timer part 363, the count value tcount when the falling edge was detected, and substitutes the obtained the count value tcount for the fall time tdown. Note that the fall time tdown is a variable stored in the memory 806 such as a RAM inside the CPU 80.

In step S207, the CPU 80 determines based on the fall time tdown whether or not the polar characters match (whether or not the connection state is the basic connection state). For example, the comparison part 801 of the CPU 80 determines whether or not the fall time tdown is smaller than the threshold t_th1. As shown in FIG. 7B and FIG. 7D, the fall time tdown of the basic connection state is shorter than the fall time tdown in the reverse connection state. Accordingly, when it is assumed that a mean value of the both values is the threshold t_th1, the CPU 80 can distinguish between the basic connection state and the reverse connection state from the fall times tdown. If the polar characters match (if the connection state is the basic connection state), the process proceeds to step S208. In step S208, the change part 802 of the CPU 80 writes "0" in the polar character bit. On the other hand, if it is determined in step S207 that the polar characters do not match, the process proceeds to step S209.

In step S209, the CPU 80 executes malfunction determination. For example, the malfunction detection part 805 of the CPU 80 determines whether or not the fall time tdown is greater than or equal to the threshold t_th1 and is smaller than a threshold t_th2. The threshold t_th2 is a threshold defined in advance as a determination criterion for a malfunction. When it is determined based on the fall time tdown that a malfunction has not occurred, the process proceeds to step S210. In step S210, the change part 802 of the CPU 80 writes "1" in the polar character bit. On the other hand, when it is determined based on the fall time tdown that a malfunction has occurred, the process proceeds to step S211. In step S211, the CPU 80 executes the above-described malfunction processing.

Figure 10:
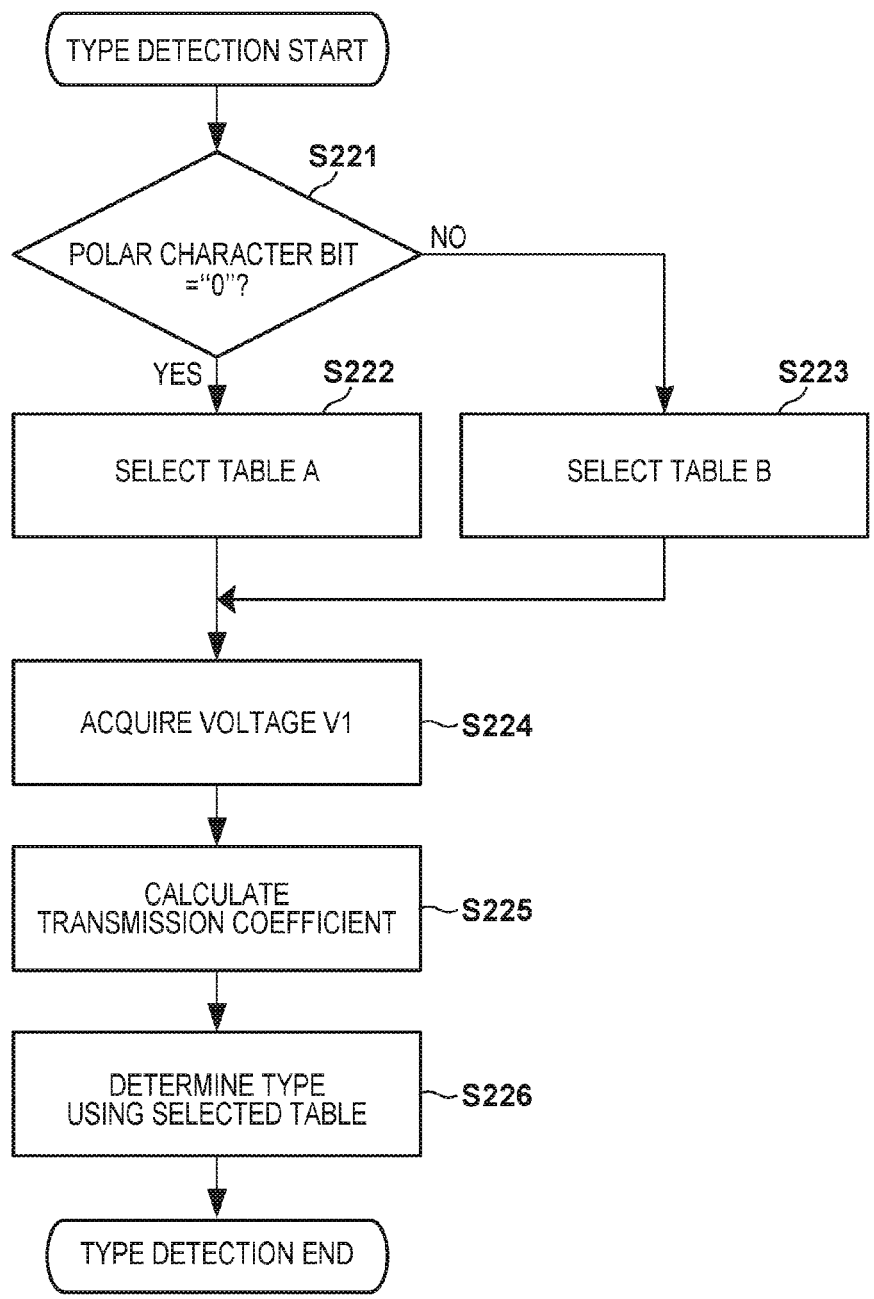
FIG. 10 is a flowchart showing processing for detecting the type of a recording medium.

FIG. 10 is a flowchart showing each step of a type detection method. The CPU 80 starts this processing when the recording medium P is fed to a conveyance path. In step S221, the change part 802 of the CPU 80 determines based on the polar character bit whether the connection state is the basic connection state or the reverse connection state. For example, the CPU 80 determines whether or not the polar character bit is "0". If the polar character bit is "0", the connection state is the basic connection state, and therefore the CPU 80 proceeds the process to step S222. In step S222, the change part 802 of the CPU 80 selects the table A for the basic connection state. On the other hand, if the polar character bit is "1", the connection state is the reverse connection state, and therefore the CPU 80 proceeds the process to step S223. In step S223, the change part 802 of the CPU 80 selects the table B for the reverse connection state. It is assumed that the tables A and B are stored in the memory 806 in advance.

In step S224, the determination part 803 of the CPU 80 acquires the voltage V1. For example, the determination part 803 uses the timer part 363 to measure the fall time tdown, and acquires, through the sensor control part 30, the voltage V1 when the count value matches the fall time tdown. As shown in FIG. 7B, the voltage V1 in the basic connection state is the voltage Va acquired at the timing G. As shown in FIG. 7D, the voltage V1 in the reverse connection state is the voltage Vb acquired at the timing H.

In step S225, the determination part 803 of the CPU 80 calculates the transmission coefficient c from the voltage V1. The calculating method of the transmission coefficient c is as described above. In step S226, the determination part 803 of the CPU 80 determines the type of the recording medium P (grammage) using the selected table and the transmission coefficient c. The setting part 808 of the CPU 80 adjusts image forming conditions and the like in accordance with the determined type.

According to the present embodiment, the polar character parameter is acquired from the reception signal of an ultrasonic wave, and the determination scheme for a recording medium is changed (table is switched) in accordance with the polar character parameter. In particular, the fall time Tg of the zero cross signal was illustrated as the polar character parameter. Accordingly, because the necessity of managing each polar character of the transmission part 31 and the reception part 32 of the ultrasonic wave while assembling the components during manufacture is eliminated, the cost of the determination apparatus can be reduced.

Summary

As described above, the transmission part 31 is one example of a transmission unit which has two terminals having a polar character, and transmits an ultrasonic wave due to a drive signal being supplied to the two terminals. The reception part 32 is one example of a reception unit which has two terminals having a polar character, receives the ultrasonic wave transmitted from the transmission part 31, and outputs a reception signal from the two terminals in accordance with the received ultrasonic wave. The change part 802 of the CPU 80 changes the determination scheme for determining the type (e.g., a grammage, a thickness and the like) of the recording medium P based on the polar character parameter acquired from the reception signal Sr output by the reception part 32 receiving the ultrasonic wave. The polar character parameter is information indicating the relation between the polar character of the transmission part 31 that transmits the ultrasonic wave and the polar character of the reception part 32 that receives the ultrasonic wave. In this manner, according to the present invention, the polar character parameter is acquired from the reception signal Sr of the ultrasonic wave, and the determination scheme for the recording medium P is changed in accordance with the polar character parameter. Accordingly, because the necessity of managing each polar character of the transmission part 31 and the reception part 32 of the ultrasonic wave while assembling the components during manufacture is eliminated, the cost of the determination apparatus can be reduced. Note that although description was given in which the determination apparatus in the present embodiment is constituted by the grammage sensor 40, the CPU 80, and the like, the sensor control part 30 may have the functions of the CPU 80. Moreover, the change part 802 of the CPU 80 functions as an acquiring unit that acquires the polar character parameter from the reception signal Sr.

As described with reference to FIG. 4A and the like, the transmission part 31 and the reception part 32 may individually have a mutual transformation member (e.g., the piezoelectric element 330 or the like) that mutually transforms between an electrical signal and an ultrasonic wave and has a polar character. Because the output terminal of the piezoelectric element 330 has a polar character, the above-described problem occurs when the ultrasonic wave sensor or the grammage sensor 40 is assembled without managing polar characters.

There are various methods for determining the type of the recording medium P. For example, the determination part 803 obtains the transmission coefficient c of the ultrasonic wave from the amplitude of the reception signal acquired when the recording medium P is not being conveyed between the transmission part 31 and the reception part 32 (the voltage V0) and the amplitude of the reception signal acquired when the recording medium P is being conveyed between the transmission part 31 and the reception part 32 (the voltage V1). As described with reference to FIG. 8 and the like, the determination part 803 determines the type of the recording medium P based on the transmission coefficient c.

As described with reference to FIG. 2 and FIG. 6, the drive signal generation part 331 functions as a generation unit that generates the drive signal Sb for driving the transmission part 31. As described with reference to FIG. 4B, FIG. 4D, and the like, the polar character parameters include the amplitude of the reception signal Sr output from the reception part 32 at the timing D when the predetermined time has elapsed from the timing when the transmission of the ultrasonic wave from the transmission part 31 was started, and the like. The comparison part 801 of the CPU 80 compares the voltage V1, which is the amplitude at the timing D, with the threshold Vth. Furthermore, the change part 802 may change the drive signal Sb in accordance with the comparison result of the comparison part 801. As described with reference to FIG. 4F, the drive signal Sb is a pulse signal that repeatedly changes between a high level and a low level. The change part 802 reverses the high level and the low level of the pulse signal if the amplitude of the reception signal Sr acquired at the timing D does not exceed the threshold Vth. This is because the polar characters of the transmission part 31 and the reception part 32 do not match. Moreover, the change part 802 does not change the pulse signal if the amplitude of the reception signal Sr exceeds the threshold Vth. This is because the polar characters of the transmission part 31 and the reception part 32 match. In accordance with whether or not the polar characters of the transmission part 31 and the reception part 32 match in this manner, the pulse signal starting at the low level and the pulse signal starting at the high level are switched. Changing the drive signal in accordance with the polar characters (connection state) in this manner makes it possible to change the determination scheme.

As described with respect to step S109 and step S111, the malfunction detection part 805 may detect a malfunction of the transmission part 31 or the reception part 32. The malfunction detection part 805 acquires the amplitude of the reception signal (the voltage V2) output from the reception part 32 at the timing D when the predetermined time has elapsed from the timing when the transmission of the ultrasonic wave from the transmission part 31 was started in accordance with the pulse signal whose level was reversed between the high level and the low level. If the voltage V2 still does not exceed the threshold Vth, the CPU 80 determines that a malfunction has occurred in the transmission part 31 or the reception part 32. Accordingly, it becomes possible to detect a malfunction of the transmission part 31 or the reception part 32. Therefore, it will be possible to suppress setting of the wrong image forming conditions based on an erroneous determination result caused by a malfunction.

Incidentally, the propagation time of an ultrasonic wave has temperature dependency. In view of this, the environment sensor 35 functioning as a temperature detection unit may detect an environmental temperature of the determination apparatus. The computing part 807 may compute the predetermined time Tg or the timing D based on the environmental temperature. Accordingly, it becomes possible to precisely determine the predetermined time Tg and the timing D in accordance with the environmental temperature.

As described in the second embodiment, the zero cross detection part 361 detects the zero cross of the reception signal Sr output by the reception part 32, and outputs the zero cross signal Se. The comparison part 801 of the CPU 80 compares, with the first threshold t_th1, the elapsed time from the timing when the transmission of the ultrasonic wave from the transmission part 31 was started until the falling timing of the zero cross signal (the fall time tdown). The change part 802 changes the determination scheme for determining the type of the recording medium P in accordance with the comparison result regarding the elapsed time tdown (the fall time tdown), which is a polar character parameter. In this manner, a polar character parameter may be the elapsed time from the timing when the transmission of the ultrasonic wave was started until the falling timing of the zero cross signal. Note that, in the second embodiment, the first falling of the zero cross signal is detected but this is merely one example. For example, the CPU 80 may compare, with the first threshold, an elapsed time (fall time tdown) after the predetermined time Tg elapsed and from the timing when the transmission of the ultrasonic wave was started until the number of times of detection of the zero cross (e.g., the number of times of detection of the falling of the zero cross signal) reached a predetermined number of times.

As described with reference to FIG. 8, the memory 806 of the CPU 80 may store a plurality of tables in which the relation between the transmission coefficient of the ultrasonic wave and the type of the recording medium is registered. The memory 806 may be a storage such as a RAM, a ROM, or a hard disk drive apparatus, for example. As described with reference to FIG. 9 and FIG. 10, the change part 802 selects a first table among the plurality of tables if the fall time tdown is smaller than the first threshold. The change part 802 selects a second table among the plurality of tables if the fall time tdown is not smaller than the first threshold. In this manner, the plurality of tables are provided in a storage such as the memory 806 in advance, and the tables are switched in accordance with the fall time tdown. Accordingly, an appropriate table is selected in accordance with the polar characters. That is, the necessity of managing the polar characters of the transmission part 31 and the reception part 32 during assembly is eliminated.

The malfunction detection part 805 may detect a malfunction of the transmission part 31 or the reception part 32 in accordance with whether or not the fall time tdown exceeds the second threshold t_th2 that is greater than the first threshold. Accordingly, it becomes possible to detect the malfunction of the transmission part 31 or the reception part 32. Therefore, it will be possible to suppress setting of the wrong image forming conditions based on an erroneous determination result caused by a malfunction.

The timer part 363 may function as a measuring unit that measures an elapsed time from a timing when the transmission of the ultrasonic wave from the transmission part 31 was started. As described with reference to FIG. 7B and FIG. 7D, the zero cross detection part 361 starts detection of a zero cross when the elapsed time exceeds the predetermined time Tg. Accordingly, it will be possible to precisely detect the zero cross in consideration of the response property of the reception part 32.

As described with reference to FIG. 6, the peak hold part 362 for holding the peak of the amplitude of the reception signal may be provided. The determination part 803 of the CPU 80 may obtain the transmission coefficient of the ultrasonic wave for determining the type of the recording medium P based on the peak-held amplitude.

Moreover, the setting part 808 of the CPU 80 may set image forming conditions (a conveying condition, a transfer condition, a fixing condition and the like) based on the determination result of the determination part 803. The CPU 80 controls an image forming engine for forming an image on the recording medium P in accordance with the image forming conditions set by the setting part 808. Accordingly, it will be possible to appropriately adjust a conveying property, a transfer property, a fixing property and the like in accordance with the type of the recording medium P.

As described above, the voltages of the detection signal Sd at the timing D and the fall time tdown were illustrated as polar character parameters. However, other parameters may be adopted as long as they are polar character parameters enabling the detection of matching or mismatching of the polar characters of the transmission part 31 and the reception part 32.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-188250, filed Sep. 16, 2014 which is hereby incorporated by reference wherein in its entirety.

What is claimed is:

1. A determination apparatus comprising:
 a transmission control unit including two terminals having a different polar character and configured to output a drive signal from the two terminals;

a transmission unit including two terminals having a different polar character and configured to transmit an ultrasonic wave by input the drive signal to the two terminals;

a reception unit including two terminals having a different polar character and configured to receive the ultrasonic wave transmitted from the transmission unit and to output a reception signal from the two terminals in accordance with the received ultrasonic wave;

a reception control unit including two terminals having a different polar character and the two terminals being input the reception signal output from the reception unit, and a control unit configured to:

judge, based on the reception signal output from the reception control unit, whether or not a predetermined state occurs in which the two terminals of the transmission control unit are connected to the two terminals of the transmission unit so that each of the polar characters matches and the two terminals of the reception control unit are connected to the two terminals of the reception unit so that each of the polar characters mismatches, or the two terminals of the transmission control unit connected to the two terminals of the transmission unit so that each of the polar characters mismatches and the two terminals of the reception control unit are connected to the two terminals of the reception unit so that each of the polar characters matches; and reverse a waveform of the reception signal in a case that the control unit judges that the predetermined state has occurred; and determine a type of a recording medium based on an amplitude of the reception signal of which the waveform is reversed by the control unit, the reception signal being acquired during the recording medium conveyed between the transmission unit and the reception unit.

2. The determination apparatus according to claim 1, wherein the control unit is further configured not to reverse the waveform of the reception signal in a case that the control unit judges that the predetermined state does not occur and a different state occurs in which the two terminals of the transmission control unit are connected to the two terminals of the transmission unit so that each of the polar characters matches and the two terminals of the reception control unit are connected to the two terminals of the reception unit so that each of the polar characters matches, or the two terminals of the transmission control unit are connected to the two terminals of the transmission unit so that each of the polar characters mismatches and the two terminals of the reception control unit are connected to the two terminals of the reception unit so that each of the polar characters mismatches, and wherein the control unit is further configured to determine the type of the recording medium based on an amplitude of the reception signal of which the waveform is not reversed by the control unit, the reception signal being acquired during the recording medium conveyed between the transmission unit and the reception unit.

3. The determination apparatus according to claim 2, wherein the control unit is further configured to reverse the waveform of the reception signal by reversing a waveform of the drive signal output from the transmission control unit.

4. The determination apparatus according to claim 3, wherein the drive signal is a pulse signal of which level repeatedly changes between a high level and a low level, and the control unit is further configured to reverse the waveform of the reception signal by reversing the high level and the low level of the pulse signal.

5. The determination apparatus according to claim 4, wherein the control unit is further configured to judge that the predetermined state has occurred, in a case that an amplitude of the reception signal acquired at a timing when a predetermined time has elapsed from a timing when transmission of the ultrasonic wave from the transmission unit was started does not exceed a threshold, and to judge that the different state has occurred in a case that the amplitude of the reception signal exceeds the threshold.

6. The determination apparatus according to claim 5, wherein the control unit is further configured to determine the type of the recording medium based on the amplitude of the reception signal of which the waveform is reversed by the control unit, the reception signal being acquired at the timing when the predetermined time has elapsed from the timing when transmission of the ultrasonic wave from the transmission unit was started.

7. The determination apparatus according to claim 5, wherein the control unit is further configured to detect a malfunction of the transmission unit or the reception unit, in a case that the amplitude of the reception signal of which the waveform is reversed by the control unit does not exceed the threshold, the reception signal being acquired at the timing when the predetermined time has elapsed from the timing when transmission of the ultrasonic wave from the transmission unit was started.

8. The determination apparatus according to claim 5, further comprising:

a temperature detection unit configured to detect an environmental temperature of the determination apparatus; and wherein the control unit is further configured to compute the predetermined time based on the environmental temperature.

9. The determination apparatus according to claim 1, wherein the transmission unit and the reception unit each have a mutual transformation member including two terminals having a polar character configured to mutually transform between an electrical signal and an ultrasonic wave.

10. The determination apparatus according to claim 9, wherein the mutual transformation member is a piezoelectric element.

11. The determination apparatus according to claim 1, wherein the control unit is further configured to obtain a transmission coefficient of the ultrasonic wave from an amplitude of the reception signal acquired when the recording medium is not being conveyed between the transmission unit and the reception unit and an amplitude of the reception signal acquired when the recording medium is being conveyed between the transmission unit and the reception unit, and determine the type of the recording medium based on the transmission coefficient.

12. The determination apparatus according to claim 1, wherein the type of the recording medium is a thickness or a grammage.

13. A determination apparatus comprising:
a transmission control unit including two terminals having a different polar character and configured to output a drive signal from the two terminals;
a transmission unit including two terminals having a different polar character and configured to transmit an ultrasonic wave by input the drive signal to the two terminals;
a reception unit including two terminals having a different polar character and configured to receive the ultrasonic wave transmitted from the transmission unit and to output a reception signal from the two terminals in accordance with the received ultrasonic wave;
a reception control unit including two terminals having a different polar character and the two terminals being input the reception signal output from the reception unit;
a storage unit configured to store a plurality of information to be used for determination of a type of a recording medium; and
a control unit configured to:
judge, based on the reception signal output from the reception control unit, whether a first state or a second state occurs, the first state being a state in which the two terminals of the transmission control unit are connected to the two terminals of the transmission unit so that each of the polar characters matches and the two terminals of the reception control unit are connected to the two terminals of the reception unit so that each of the polar characters matches, or the two terminals of the transmission control unit are connected to the two terminals of the transmission unit so that each of the polar characters mismatches and the two terminals of the reception control unit are connected to the two terminals of the reception unit so that each of the polar characters mismatches, and the second state being a state in which the two terminals of the transmission control unit are connected to the two terminals of the transmission unit so that each of the polar characters matches and the two terminals of the reception control unit are connected to the two terminals of the reception unit so that each of the polar characters mismatches, or the two terminals of the transmission control unit are connected to the two terminals of the transmission unit so that each of the polar characters mismatches and the two terminals of the reception control unit are connected to the two terminals of the reception unit so that each of the polar characters matches;
select a first information from the plurality of information stored in the storage unit in a case that the control unit judges that the first state has occurred and select a second information from the plurality of information stored in the storage unit in a case that the control unit judges that the second state has occurred; and
determine a type of a recording medium based on information selected by the control unit and an amplitude of the reception signal acquired during the recording medium conveyed between the transmission unit and the reception unit.

14. The determination apparatus according to claim 13, wherein the plurality of information stored in the storage unit is a plurality of tables in which a relation between the amplitude of the reception signal and the type of the recording medium is registered,
wherein the control unit is further configured to select a first table among the plurality of tables in the case that the control unit judges that the first state has occurred and select a second table among the plurality of tables in the case that the control unit judges that the second state has occurred.

15. The determination apparatus according to claim 14, wherein the reception control unit is further configured to detect a zero cross of the reception signal output by the reception unit and to output a zero cross signal; and
wherein the control unit is further configured to judge that the first state occurs in a case that an elapsed time from a timing when transmission of the ultrasonic wave from the transmission unit was started until a falling timing of the zero cross signal is shorter than a first threshold, and judge that the second state occurs in a case that the elapsed time is longer than the first threshold.

16. The determination apparatus according to claim 15, wherein the control unit is further configured to detect a malfunction of the transmission unit or the reception unit in a case that the elapsed time exceeds a second threshold that is greater than the first threshold.

17. The determination apparatus according to claim 15, wherein the reception control unit is further configured to measure an elapsed time from the timing when transmission of the ultrasonic wave from the transmission unit was started,
wherein the reception control unit is further configured to start detection of the zero cross when the elapsed time exceeds a predetermined time.

18. The determination apparatus according to claim 15, wherein the reception control unit is further configured to hold a peak of an amplitude of the reception signal,
wherein the control unit is further configured to determine the type of the recording medium based on the table selected by the control unit and the amplitude of the reception signal acquired at a fall timing of the zero cross signal.

19. The determination apparatus according to claim 13, wherein the transmission unit and the reception unit each have a mutual transformation member including two terminals having a polar character configured to mutually transform between an electrical signal and an ultrasonic wave.

20. The determination apparatus according to claim 19, wherein the mutual transformation member is a piezoelectric element.

21. The determination apparatus according to claim 13, wherein the control unit is further configured to obtain a transmission coefficient of the ultrasonic wave from an amplitude of the reception signal acquired when the recording medium is not being conveyed between the transmission unit and the reception unit and an amplitude of the reception signal acquired when the recording medium is being conveyed between the transmission unit and the reception unit, and determine the type of the recording medium based on the transmission coefficient.

22. The determination apparatus according to claim 13, wherein the type of the recording medium is a thickness or a grammage.

23. An image forming apparatus comprising:
an image formation unit configured to form an image on a recording medium;
a transmission control unit including two terminals having a different polar character and configured to output a drive signal from the two terminals;

a transmission unit including two terminals having a different polar character and configured to transmit an ultrasonic wave by input the drive signal to the two terminals;

a reception unit including two terminals having a different polar character and configured to receive the ultrasonic wave transmitted from the transmission unit and to output a reception signal from the two terminals in accordance with the received ultrasonic wave;

a reception control unit including two terminals having a different polar character and the two terminals being input the reception signal output from the reception unit;

a control unit configured to:

judge, based on the reception signal output from the reception control unit, whether or not a predetermined state occurs in which the two terminals of the transmission control unit are connected to the two terminals of the transmission unit so that each of the polar characters matches and the two terminals of the reception control unit are connected to the two terminals of the reception unit so that each of the polar characters mismatches, or the two terminals of the transmission control unit are connected to the two terminals of the transmission unit so that each of the polar characters mismatches and the two terminals of the reception control unit are connected to the two terminals of the reception unit so that each of the polar characters matches;

reverse a waveform of the reception signal in a case that the control unit judges that the predetermined state has occurred; and set an image forming condition of the image formation unit based on an amplitude of the reception signal of which the waveform is reversed by the control unit, the reception signal being acquired during the recording medium conveyed between the transmission unit and the reception unit.

24. An image forming apparatus comprising:

an image formation unit configured to form an image on a recording medium;

a transmission control unit including two terminals having a different polar character and configured to output a drive signal from the two terminals;

a transmission unit including two terminals having a different polar character and configured to transmit an ultrasonic wave by input the drive signal to the two terminals;

a reception unit including two terminals having a different polar character and configured to receive the ultrasonic wave transmitted from the transmission unit and to output a reception signal from the two terminals in accordance with the received ultrasonic wave;

a reception control unit including two terminals having a different polar character and the two terminals being input the reception signal output from the reception unit;

a storage unit configured to store a plurality of information to be used for determination of a type of a recording medium;

a control unit configured to judge, based on the reception signal output from the reception control unit, whether a first state or a second state occurs, the first state being a state in which the two terminals of the transmission control unit are connected to the two terminals of the transmission unit so that each of the polar characters matches and the two terminals of the reception control unit are connected to the two terminals of the reception unit so that each of the polar characters matches, or the two terminals of the transmission control unit are connected to the two terminals of the transmission unit so that each of the polar characters mismatches and the two terminals of the reception control unit are connected to the two terminals of the reception unit so that each of the polar characters mismatches, and the second state being a state in which the two terminals of the transmission control unit are connected to the two terminals of the transmission unit so that each of the polar characters matches and the two terminals of the reception control unit are connected to the two terminals of the reception unit so that each of the polar characters mismatches, or the two terminals of the transmission control unit are connected to the two terminals of the transmission unit so that each of the polar characters mismatches and the two terminals of the reception control unit are connected to the two terminals of the reception unit so that each of the polar characters matches;

select a first information from the plurality of information stored in the storage unit in a case that the control unit judges that the first state has occurred and select a second information from the plurality of information stored in the storage unit in a case that the control unit judges that the second state has occurred; and set an image forming condition of the image formation unit based on information selected by the control unit and an amplitude of the reception signal being acquired during the recording medium conveyed between the transmission unit and the reception unit.

* * * * *